United States Patent [19]

Leisy et al.

[11] Patent Number: 5,470,735
[45] Date of Patent: Nov. 28, 1995

[54] INSECTICIDAL PLECTOXINS FROM PLECTREURYS TRISTIS

[75] Inventors: Douglas J. Leisy, Palo Alto; Gary B. Quistad, Mountain View; Wayne S. Skinner, Portola Valley, all of Calif.

[73] Assignee: Sandoz Ltd., Basel, Switzerland

[21] Appl. No.: 221,285

[22] Filed: Mar. 30, 1994

Related U.S. Application Data

[63] Continuation of Ser. No. 163,602, Dec. 6, 1993, abandoned, which is a continuation of Ser. No. 58,051, May 3, 1993, abandoned, which is a continuation of Ser. No. 837,194, Feb. 11, 1992, abandoned.

[51] Int. Cl.[6] .......................... C12N 7/01; C12N 15/63; C12N 15/12; A61K 45/00
[52] U.S. Cl. .................. 435/235.1; 435/320.1; 424/936; 536/23.5; 935/57
[58] Field of Search .................. 536/23.5; 424/93 T, 424/93.6; 435/235.1, 320.1; 935/57

[56] References Cited

U.S. PATENT DOCUMENTS 4,745,051  5/1988  Smith et al. .................. 435/69.51
5,041,379  8/1991  Fraser et al. .................. 435/235.1

OTHER PUBLICATIONS

Branton et al. 1987. "Neurotoxins from *Plectreurys* Spider Venom are Potent Presynaptic Blockers in *Drosophila*" *J. Neurosci.* 7(12) 4195–4200.

Jackson et al. 1986. "Effects of Spider Venoms on Transmission Mediated by Non-N-Methyl-D-Aspartate Receptors" *Excitatory Amino Acid Transmission* Hicks et al. Eds. Alan R. Liss, Inc., NY 51–54.

Branton et al. (1993) Nature 365: 498–499.

*Primary Examiner*—Robert A. Wax
*Assistant Examiner*—G. E. Bugaisky
*Attorney, Agent, or Firm*—Lynn Marcus-Wyner; Allen E. Norris

[57] ABSTRACT

Novel plectoxins isolated from the Primitive Hunting Spider, *Plectreurys tristis* are described, and their amino acid sequences are presented. These are toxic to various groups of insects, including Lepidopterans. A particularly potent plectoxin is Plt-VI. The plectoxins may be cloned into a baculovirus vector and hasten its speed of kill.

8 Claims, 6 Drawing Sheets

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Modified-site
        ( B ) LOCATION: 1..24
        ( D ) OTHER INFORMATION: /label=XAA
            / note="AA1=A or E; AA2=V OR L; AA5=I OR Q; AA8=Q
            OR V; AA9=E OR D; AA10=T OR Y; AA12=N OR R; AA14=N
            OR K; AA15=L OY V; AA16=P OR E; AA19=N OR D;

( x i ) SEQUENCE DESCRIPTION: SEQ ID NO:1:

```
Xaa  Xaa  Lys  Cys  Xaa  Gly  Trp  Xaa  Xaa  Xaa  Cys  Xaa  Gly  Xaa  Xaa  Xaa
 1                   5                           10                          15

Cys  Cys  Xaa  Xaa  Cys  Val  Met  Xaa
               20
```

( 2 ) INFORMATION FOR SEQ ID NO:2:

( i ) SEQUENCE CHARACTERISTICS:
  ( A ) LENGTH: 18 amino acids
  ( B ) TYPE: amino acid
  ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
  ( A ) NAME/KEY: Modified-site
  ( B ) LOCATION: 15..18
  ( D ) OTHER INFORMATION: /label=XAA
    / note="AA39=K OR R; AA40=A,M, OR I; AA42=N OR S"

( x i ) SEQUENCE DESCRIPTION: SEQ ID NO:2:

Glu Cys Asn Ile Met Gly Gln Asn Cys Arg Cys Asn His Pro Xaa Xaa
1               5                   10                  15

Thr Xaa ( 2 ) INFORMATION FOR SEQ ID NO:3:

( i ) SEQUENCE CHARACTERISTICS:
    ( A ) LENGTH: 46 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:3:

Cys Ala Lys His Ser Glu Thr Cys Lys Asn Gly Asn Cys Cys Thr Cys
1               5                   10                  15

Thr Gln Tyr Arg Gly Lys Asp Glu Pro Met Ala Cys Arg Arg Gly Thr
            20                  25                  30

His Gly Gln Arg Cys Gln Cys Val Met Lys Ile Met Lys His
        35                  40                  45

( 2 ) INFORMATION FOR SEQ ID NO:4:

( i ) SEQUENCE CHARACTERISTICS:
    ( A ) LENGTH: 49 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:4:

Gly Cys Lys Gly Phe Leu Val Lys Cys Asp Ser Asn Ser Glu Cys Cys
1               5                   10                  15

Lys Thr Ala Ile Val Lys Gly Lys Lys Gln Leu Ser Cys Leu Cys
            20                  25                  30

Gly Ala Trp Gly Ala Gly Cys Ser Cys Ser Phe Arg Cys Gly Asn Arg
            35                  40                  45

Cys ( 2 ) INFORMATION FOR SEQ ID NO:5:

( i ) SEQUENCE CHARACTERISTICS:
        ( A ) LENGTH: 46 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:5:

```
Ala  Val  Lys  Cys  Ile  Gly  Trp  Gln  Glu  Thr  Cys  Asn  Gly  Asn  Leu  Pro
 1                    5                        10                       15

Cys  Cys  Asn  Glu  Cys  Val  Met  Cys  Glu  Cys  Asn  Ile  Met  Gly  Gln  Asn
              20                        25                       30

Cys  Arg  Cys  Asn  His  Pro  Lys  Ala  Thr  Asn  Glu  Cys  Glu  Ser
          35                        40                       45
```

( 2 ) INFORMATION FOR SEQ ID NO:6:

( i ) SEQUENCE CHARACTERISTICS:
        ( A ) LENGTH: 46 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:6:

```
Ala  Val  Lys  Cys  Ile  Gly  Trp  Gln  Glu  Thr  Cys  Asn  Gly  Lys  Leu  Pro
 1                    5                        10                       15

Cys  Cys  Asp  Gly  Cys  Val  Met  Cys  Glu  Cys  Asn  Ile  Met  Gly  Gln  Asn
              20                        25                       30

Cys  Arg  Cys  Asn  His  Pro  Lys  Met  Thr  Ser  Glu  Cys  Gly  Ser
          35                        40                       45
```

( 2 ) INFORMATION FOR SEQ ID NO:7:

( i ) SEQUENCE CHARACTERISTICS:
        ( A ) LENGTH: 46 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:7:

```
Glu  Val  Lys  Cys  Ile  Gly  Trp  Gln  Glu  Tyr  Cys  Arg  Gly  Asn  Leu  Pro
 1                    5                        10                       15

Cys  Cys  Asp  Asp  Cys  Val  Met  Cys  Glu  Cys  Asn  Ile  Met  Gly  Gln  Asn
              20                        25                       30

Cys  Arg  Cys  Asn  His  Pro  Arg  Ile  Thr  Ser  Glu  Cys  Gly  Ser
          35                        40                       45
```

( 2 ) INFORMATION FOR SEQ ID NO:8:

( i ) SEQUENCE CHARACTERISTICS:
  ( A ) LENGTH: 45 amino acids
  ( B ) TYPE: amino acid
  ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:8:

```
Ala Val Lys Cys Ile Gly Trp Gln Glu Thr Cys Asn Gly Asn Leu Pro
  1               5                  10                  15
Cys Cys Asn Glu Cys Val Met Cys Glu Cys Asn Ile Met Gly Gln Asn
              20                  25                  30
Cys Arg Cys Asn His Pro Lys Ala Thr Asn Glu Cys Glu
          35                  40                  45
```

( 2 ) INFORMATION FOR SEQ ID NO:9:

( i ) SEQUENCE CHARACTERISTICS:
  ( A ) LENGTH: 24 amino acids
  ( B ) TYPE: amino acid
  ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:9:

```
Ala Leu Lys Cys Gln Gly Trp Val Asp Tyr Cys Asn Gly Asn Val Glu
  1               5                  10                  15
Cys Cys Asn Glu Cys Val Met Tyr
              20
```

( 2 ) INFORMATION FOR SEQ ID NO:10:

( i ) SEQUENCE CHARACTERISTICS:
  ( A ) LENGTH: 46 amino acids
  ( B ) TYPE: amino acid
  ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:10:

```
Ala Val Lys Cys Ile Gly Trp Gln Glu Thr Cys Asn Gly Lys Leu Pro
  1               5                  10                  15
Cys Cys Asp Gly Cys Val Met Cys Glu Cys Asn Ile Met Gly Gln Asn
              20                  25                  30
Cys Arg Cys Asn His Pro Lys Ala Thr Ser Glu Cys Glu Ser
          35                  40                  45
```

( 2 ) INFORMATION FOR SEQ ID NO:11:

( i ) SEQUENCE CHARACTERISTICS:
  ( A ) LENGTH: 7 amino acids
  ( B ) TYPE: amino acid
  ( D ) TOPOLOGY: linear ( i i ) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:11:

Ala  Thr  Asn  Glu  Cys  Glu  Ser
1                   5

(2) INFORMATION FOR SEQ ID NO:12:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:12:

GATGCGGCCG CTCRCAYTCR TTNGTNGCYT TNGG                                    34

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:13:

GATGCGGCCG CGTNAARTGU ATHGGNTGGC                                         30

(2) INFORMATION FOR SEQ ID NO:14:

(i) SEQUENCE CHARACTERISTICS:
        (A) LENGTH: 138 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: YES (i v) ANTI-SENSE: NO (x i) SEQUENCE DESCRIPTION: SEQ ID NO:14:

CGNGTNAART GYATHGGNTG GCARGARACN TGYAAYGGNA AYYTNCCNTG YTGYAAYGAR         60

TGYGTNATGT GYGARTGYAA YATHATGGGN CARAAYTGYM GNTGYAAYCA YCCNAARGCN        120

ACNAAYGART GYGARWSN                                                     138

(2) INFORMATION FOR SEQ ID NO:15:

(i) SEQUENCE CHARACTERISTICS:
        (A) LENGTH: 132 base pairs
        (B) TYPE: nucleic acid
        (C) STRANDEDNESS: single -continued ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

| GTTAAGTGTA | TTGGTTGGCA | GGAAACATGC | AACGGCAACT | TGCCCTGCTG | CAATGAGTGC | 60 |
| GTCATGTGCG | AATGCAACAT | TATGGGTCAA | AACTGCAGAT | GCAACCATCC | CGAAAGCGAC | 120 |
| CAATGAATGT | GA | | | | | 132 |

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

GGATGGTTGC ATCTGCAG                                                                                    18

( 2 ) INFORMATION FOR SEQ ID NO:17:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

GTGCAAACGA CCAATGCACA GACAAGGGCG G                                           31

( 2 ) INFORMATION FOR SEQ ID NO:18:

( i ) SEQUENCE CHARACTERISTICS:
        ( A ) LENGTH: 345 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 40..288

( x i ) SEQUENCE DESCRIPTION: SEQ ID NO:18:

GTTTTTGTAG TGAAGCACTG AGAAGCCTGT AGCAGAACC ATG AAG CAT TTG ATC    54
                                                                   Met Lys His Leu Ile
                                                                    1                  5

-continued

| | | | | | | | | | | | | | | | | |
|---|---|---|---|---|---|---|---|---|---|---|---|---|---|---|---|---|
| TTT | TCA | TCC | GCC | CTT | GTC | TGT | GCA | TTG | GTC | GTT | TGC | ACA | TTT | GCT | GAA | 102 |
| Phe | Ser | Ser | Ala | Leu | Val | Cys | Ala | Leu | Val | Val | Cys | Thr | Phe | Ala | Glu | |
| | | | | 10 | | | | | 15 | | | | | 20 | | |
| GAG | CAA | GTG | AAC | GTG | CCC | TTT | CTT | CCT | GAC | GAA | AGA | GCA | GTA | AAA | TGT | 150 |
| Glu | Gln | Val | Asn | Val | Pro | Phe | Leu | Pro | Asp | Glu | Arg | Ala | Val | Lys | Cys | |
| | | | 25 | | | | | 30 | | | | | 35 | | | |
| ATC | GGG | TGG | CAG | GAA | ACA | TGC | AAC | GGC | AAC | TTG | CCC | TGC | TGC | AAT | GAG | 198 |
| Ile | Gly | Trp | Gln | Glu | Thr | Cys | Asn | Gly | Asn | Leu | Pro | Cys | Cys | Asn | Glu | |
| | | 40 | | | | | 45 | | | | | 50 | | | | |
| TGC | GTC | ATG | TGC | GAA | TGC | AAC | ATT | ATG | GGT | CAA | AAC | TGC | AGA | TGC | AAC | 246 |
| Cys | Val | Met | Cys | Glu | Cys | Asn | Ile | Met | Gly | Gln | Asn | Cys | Arg | Cys | Asn | |
| | 55 | | | | | 60 | | | | | 65 | | | | | |
| CAT | CCC | AAA | GCA | ACT | AAC | GAA | TGC | GAG | TCA | AGA | AGG | CGT | TGAAACAGCA | | | 295 |
| His | Pro | Lys | Ala | Thr | Asn | Glu | Cys | Glu | Ser | Arg | Arg | Arg | | | | |
| 70 | | | | | 75 | | | | | 80 | | | | | | |

AAGAAATTAT CTGTATGATT TTTGGATTGA ATAAACGGGA GTAGATATGA   345

( 2 ) INFORMATION FOR SEQ ID NO:19:

( i ) SEQUENCE CHARACTERISTICS:
        ( A ) LENGTH: 82 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| | | | | | | | | | | | | | | | |
|---|---|---|---|---|---|---|---|---|---|---|---|---|---|---|---|
| Met | Lys | His | Leu | Ile | Phe | Ser | Ser | Ala | Leu | Val | Cys | Ala | Leu | Val | Val |
| 1 | | | | 5 | | | | | 10 | | | | | 15 | |
| Cys | Thr | Phe | Ala | Glu | Glu | Gln | Val | Asn | Val | Pro | Phe | Leu | Pro | Asp | Glu |
| | | | 20 | | | | | 25 | | | | | 30 | | |
| Arg | Ala | Val | Lys | Cys | Ile | Gly | Trp | Gln | Glu | Thr | Cys | Asn | Gly | Asn | Leu |
| | | 35 | | | | | 40 | | | | | 45 | | | |
| Pro | Cys | Cys | Asn | Glu | Cys | Val | Met | Cys | Glu | Cys | Asn | Ile | Met | Gly | Gln |
| | 50 | | | | | 55 | | | | | 60 | | | | |
| Asn | Cys | Arg | Cys | Asn | His | Pro | Lys | Ala | Thr | Asn | Glu | Cys | Glu | Ser | Arg |
| 65 | | | | | 70 | | | | | 75 | | | | | 80 |
| Arg | Arg | | | | | | | | | | | | | | |

( 2 ) INFORMATION FOR SEQ ID NO:20:

( i ) SEQUENCE CHARACTERISTICS:
        ( A ) LENGTH: 326 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 6..254

( x i ) SEQUENCE DESCRIPTION: SEQ ID NO:20:

| | | | | | | | | | | | | | | | | |
|---|---|---|---|---|---|---|---|---|---|---|---|---|---|---|---|---|
| GAACC | ATG | AAG | CAT | TTG | ATC | TTT | TCA | TCC | GCC | CTT | GTC | TGT | GCA | TTG | | 47 |
| | Met | Lys | His | Leu | Ile | Phe | Ser | Ser | Ala | Leu | Val | Cys | Ala | Leu | | |
| | | 1 | | | 5 | | | | | 10 | | | | | | |
| GTC | GTT | TGC | ACA | TTT | GCT | GAA | GAG | CAA | GTG | AAC | GTG | CCC | TTT | CTT | CCT | 95 |
| Val | Val | Cys | Thr | Phe | Ala | Glu | Glu | Gln | Val | Asn | Val | Pro | Phe | Leu | Pro | |
| 15 | | | | | 20 | | | | | 25 | | | | | 30 | |

| GAC | GAA | AGA | GCA | GTA | AAA | TGT | ATC | GGG | TGG | CAG | GAA | ACA | TGC | AAC | GGC | 143 |
| Asp | Glu | Arg | Ala | Val | Lys | Cys | Ile | Gly | Trp | Gln | Glu | Thr | Cys | Asn | Gly | |
| | | | | 35 | | | | | 40 | | | | | 45 | | |

| AAC | TTG | CCC | TGC | TGC | AAT | GAG | TGC | GTC | ATG | TGC | GAA | TGC | AAC | ATT | ATG | 191 |
| Asn | Leu | Pro | Cys | Cys | Asn | Glu | Cys | Val | Met | Cys | Glu | Cys | Asn | Ile | Met | |
| | | | 50 | | | | | 55 | | | | | 60 | | | |

| GGT | CAA | AAC | TGC | AGA | TGC | AAC | CAT | CCC | AAA | GCA | ACT | AAC | GAA | TGC | GAG | 239 |
| Gly | Gln | Asn | Cys | Arg | Cys | Asn | His | Pro | Lys | Ala | Thr | Asn | Glu | Cys | Glu | |
| | | 65 | | | | | 70 | | | | | 75 | | | | |

| TCA | AGA | AGG | CGT | TGAAACAGCA | AAGAAATTAT | CTGTATGATT | TTTGGATTGA | 291 |
| Ser | Arg | Arg | Arg | | | | | |
| | | 80 | | | | | | |

ATAAACGGGA GTAGATATGA CTCTGTTCGT CTGTT     326

(2) INFORMATION FOR SEQ ID NO:21:

(i) SEQUENCE CHARACTERISTICS:
        (A) LENGTH: 82 amino acids
        (B) TYPE: amino acid
        (D) TOPOLOGY: linear (ii) MOLECULE TYPE: protein (xi) SEQUENCE DESCRIPTION: SEQ ID NO:21:

| Met | Lys | His | Leu | Ile | Phe | Ser | Ser | Ala | Leu | Val | Cys | Ala | Leu | Val | Val |
| 1 | | | | 5 | | | | | 10 | | | | | 15 | |

| Cys | Thr | Phe | Ala | Glu | Glu | Gln | Val | Asn | Val | Pro | Phe | Leu | Pro | Asp | Glu |
| | | | 20 | | | | | 25 | | | | | 30 | | |

| Arg | Ala | Val | Lys | Cys | Ile | Gly | Trp | Gln | Glu | Thr | Cys | Asn | Gly | Asn | Leu |
| | | | 35 | | | | | 40 | | | | | 45 | | |

| Pro | Cys | Cys | Asn | Glu | Cys | Val | Met | Cys | Glu | Cys | Asn | Ile | Met | Gly | Gln |
| | | 50 | | | | | 55 | | | | | 60 | | | |

| Asn | Cys | Arg | Cys | Asn | His | Pro | Lys | Ala | Thr | Asn | Glu | Cys | Glu | Ser | Arg |
| 65 | | | | | 70 | | | | | 75 | | | | | 80 |

| Arg | Arg | | | | | | | | | | | | | | |

(2) INFORMATION FOR SEQ ID NO:22:

(i) SEQUENCE CHARACTERISTICS:
        (A) LENGTH: 308 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..246

(xi) SEQUENCE DESCRIPTION: SEQ ID NO:22:

| AAG | CAT | TTG | ATC | TTT | TCA | TCC | GCC | CTT | GTC | TGT | GCA | TTG | GTC | GTT | TGC | 48 |
| Lys | His | Leu | Ile | Phe | Ser | Ser | Ala | Leu | Val | Cys | Ala | Leu | Val | Val | Cys | |
| 1 | | | | 5 | | | | | 10 | | | | | 15 | | |

| ACA | TTT | GCT | GAA | GAG | CAA | GTG | AAC | GTG | CCC | TTT | CTT | CCT | GAC | GAA | AGA | 96 |
| Thr | Phe | Ala | Glu | Glu | Gln | Val | Asn | Val | Pro | Phe | Leu | Pro | Asp | Glu | Arg | |
| | | | 20 | | | | | 25 | | | | | 30 | | | |

| GCA | GTA | AAA | TGT | ATC | GGG | TGG | CAG | GAA | ACA | TGC | AAC | GGC | AAC | TTG | CCC | 144 |
| Ala | Val | Lys | Cys | Ile | Gly | Trp | Gln | Glu | Thr | Cys | Asn | Gly | Asn | Leu | Pro | |
| | | 35 | | | | | 40 | | | | | 45 | | | | |

-continued

|  |  | 35 |  |  |  | 40 |  |  |  | 45 |  |  |  |  |  |
|---|---|---|---|---|---|---|---|---|---|---|---|---|---|---|---|
| TGC | TGC | AAT | GAG | TGC | GTC | ATG | TGC | GAA | TGC | AAC | ATT | ATG | GGT | CAA | AAC | 192 |
| Cys | Cys | Asn | Glu | Cys | Val | Met | Cys | Glu | Cys | Asn | Ile | Met | Gly | Gln | Asn |
|     | 50 |     |     |     |     | 55 |     |     |     |     | 60 |

| TGC | AGA | TGC | AAC | CAT | CCC | AAA | GCA | ACT | AAC | GAA | TGC | GAG | TCA | AGA | AGG | 240 |
| Cys | Arg | Cys | Asn | His | Pro | Lys | Ala | Thr | Asn | Glu | Cys | Glu | Ser | Arg | Arg |
|  65 |     |     |     |     | 70  |     |     |     |     | 75  |     |     |     |     | 80  |

CGT TGAAACAGCA AAGAAATTAT CTGTATGATT TTTGGATTGA ATAAACGGGA    293
Arg

GTAGATATGA ATCTG    308

( 2 ) INFORMATION FOR SEQ ID NO:23:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

Lys His Leu Ile Phe Ser Ser Ala Leu Val Cys Ala Leu Val Val Cys
 1               5                  10                 15

Thr Phe Ala Glu Glu Gln Val Asn Val Pro Phe Leu Pro Asp Glu Arg
            20                  25                  30

Ala Val Lys Cys Ile Gly Trp Gln Glu Thr Cys Asn Gly Asn Leu Pro
        35                  40                  45

Cys Cys Asn Glu Cys Val Met Cys Glu Cys Asn Ile Met Gly Gln Asn
    50                  55                  60

Cys Arg Cys Asn His Pro Lys Ala Thr Asn Glu Cys Glu Ser Arg Arg
65                  70                  75                  80

Arg ( 2 ) INFORMATION FOR SEQ ID NO:24:

( i ) SEQUENCE CHARACTERISTICS:
        ( A ) LENGTH: 306 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..249

( x i ) SEQUENCE DESCRIPTION: SEQ ID NO:24:

| ATG | AAG | CAT | TTG | ATC | TTA | GCA | TCC | GCC | CTT | GTC | TGT | GCA | TTG | GTC | GTT | 48 |
| Met | Lys | His | Leu | Ile | Leu | Ala | Ser | Ala | Leu | Val | Cys | Ala | Leu | Val | Val |
|  1  |     |     |     |  5  |     |     |     |     | 10  |     |     |     |     | 15  |

| TGC | ACA | TTT | GCT | GAA | GAG | CAA | GTG | AAC | GTG | CCC | TTT | CTT | CCT | GAC | GAA | 96 |
| Cys | Thr | Phe | Ala | Glu | Glu | Gln | Val | Asn | Val | Pro | Phe | Leu | Pro | Asp | Glu |
|     |     |     | 20  |     |     |     |     | 25  |     |     |     |     | 30  |

| AGA | GCA | GTA | AAA | TGT | ATC | GGG | TGG | CAG | GAA | ACA | TGC | AAC | GGC | AAC | TTG | 144 |
| Arg | Ala | Val | Lys | Cys | Ile | Gly | Trp | Gln | Glu | Thr | Cys | Asn | Gly | Asn | Leu |
|     |     |     | 35  |     |     |     |     | 40  |     |     |     |     | 45  |

| CCC | TGC | TGC | AAT | GAG | TGC | GTC | ATG | TGC | GAA | TGC | AAC | ATT | ATG | GGT | CAA | 192 |
| Pro | Cys | Cys | Asn | Glu | Cys | Val | Met | Cys | Glu | Cys | Asn | Ile | Met | Gly | Gln |

```
                  50                          55                          60
AAC  TGC  AGA  TGC  AAC  CAT  CCC  AAA  GCA  ACT  AAC  GAA  TGC  GAG  TCA  AGA    240
Asn  Cys  Arg  Cys  Asn  His  Pro  Lys  Ala  Thr  Asn  Glu  Cys  Glu  Ser  Arg
 65                      70                          75                      80

AGG  CGT  TGAAACAGCA   AAGAAATTAT   CTGTATGATT   TTTGGATTGA   ATAAACGGGA          296
Arg  Arg

GTAGATATGA                                                                        306
```

( 2 ) INFORMATION FOR SEQ ID NO:25:

( i ) SEQUENCE CHARACTERISTICS:
        ( A ) LENGTH: 82 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Met  Lys  His  Leu  Ile  Leu  Ala  Ser  Ala  Leu  Val  Cys  Ala  Leu  Val  Val
 1                   5                        10                       15

Cys  Thr  Phe  Ala  Glu  Glu  Gln  Val  Asn  Val  Pro  Phe  Leu  Pro  Asp  Glu
               20                       25                        30

Arg  Ala  Val  Lys  Cys  Ile  Gly  Trp  Gln  Glu  Thr  Cys  Asn  Gly  Asn  Leu
               35                        40                       45

Pro  Cys  Cys  Asn  Glu  Cys  Val  Met  Cys  Glu  Cys  Asn  Ile  Met  Gly  Gln
      50                        55                        60

Asn  Cys  Arg  Cys  Asn  His  Pro  Lys  Ala  Thr  Asn  Glu  Cys  Glu  Ser  Arg
 65                      70                          75                      80

Arg  Arg
```

( 2 ) INFORMATION FOR SEQ ID NO:26:

( i ) SEQUENCE CHARACTERISTICS:
        ( A ) LENGTH: 302 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 3..245

( x i ) SEQUENCE DESCRIPTION: SEQ ID NO:26:

```
AG   CAT  TTG  ATC  TTA  GCA  TCC  GCC  CTT  ATC  TGT  GCA  TTG  GTC  GTT  TGC    47
     His  Leu  Ile  Leu  Ala  Ser  Ala  Leu  Ile  Cys  Ala  Leu  Val  Val  Cys
      1                   5                        10                       15

ACA  TCT  GCT  GAA  GAG  CAA  GTG  AAC  GTG  CCC  TTT  CTT  CCT  GAC  GAA  AGA    95
Thr  Ser  Ala  Glu  Glu  Gln  Val  Asn  Val  Pro  Phe  Leu  Pro  Asp  Glu  Arg
               20                        25                       30

GCA  GTA  AAA  TGT  ATC  GGG  TGG  CAG  GAA  ACA  TGC  AAC  GGC  AAC  TTG  CCC   143
Ala  Val  Lys  Cys  Ile  Gly  Trp  Gln  Glu  Thr  Cys  Asn  Gly  Asn  Leu  Pro
               35                        40                       45

TGC  TGC  AAT  GAG  TGC  GTC  ATG  TGC  GAA  TGC  AAC  ATT  ATG  GGT  CAA  AAC   191
Cys  Cys  Asn  Glu  Cys  Val  Met  Cys  Glu  Cys  Asn  Ile  Met  Gly  Gln  Asn
      50                        55                        60

TGC  AGA  TGC  AAC  CAT  CCC  AAA  GCA  ACT  AAC  GAA  TGC  GAG  TCA  AGA  AGG   239
Cys  Arg  Cys  Asn  His  Pro  Lys  Ala  Thr  Asn  Glu  Cys  Glu  Ser  Arg  Arg
```

```
                 65                      70                     75
CGT  TGAAACAGCA  AAGAAATTAT  CTGTATGATT  TTTGGATTGA  ATAAACGGGA              292
Arg
 80

GTAGATATGA                                                                   302
```

( 2 ) INFORMATION FOR SEQ ID NO:27:

( i ) SEQUENCE CHARACTERISTICS:
    ( A ) LENGTH: 80 amino acids
    ( B ) TYPE: amino acid
    ( D ) TOPOLOGY: linear ( i i ) MOLECULE TYPE: protein ( x i ) SEQUENCE DESCRIPTION: SEQ ID NO:27:

```
His  Leu  Ile  Leu  Ala  Ser  Ala  Leu  Ile  Cys  Ala  Leu  Val  Val  Cys  Thr
 1              5                        10                       15

Ser  Ala  Glu  Glu  Gln  Val  Asn  Val  Pro  Phe  Leu  Pro  Asp  Glu  Arg  Ala
               20                       25                       30

Val  Lys  Cys  Ile  Gly  Trp  Gln  Glu  Thr  Cys  Asn  Gly  Asn  Leu  Pro  Cys
          35                       40                       45

Cys  Asn  Glu  Cys  Val  Met  Cys  Glu  Cys  Asn  Ile  Met  Gly  Gln  Asn  Cys
     50                       55                       60

Arg  Cys  Asn  His  Pro  Lys  Ala  Thr  Asn  Glu  Cys  Glu  Ser  Arg  Arg  Arg
65                       70                       75                       80
```

( 2 ) INFORMATION FOR SEQ ID NO:28:

( i ) SEQUENCE CHARACTERISTICS:
    ( A ) LENGTH: 312 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: CDS
    ( B ) LOCATION: 7..255

( x i ) SEQUENCE DESCRIPTION: SEQ ID NO:28:

```
AGAACC  ATG  AAG  CAT  TTG  ATC  TTA  GCA  TCC  GCC  CTT  ATC  TGT  GCA  TTG       48
        Met  Lys  His  Leu  Ile  Leu  Ala  Ser  Ala  Leu  Ile  Cys  Ala  Leu
         1             5                            10

GTC  GTT  TGC  ACA  TCT  GCT  GAA  GAG  CAA  GTG  AAC  GTG  CCC  TTT  CTT  CCT     96
Val  Val  Cys  Thr  Ser  Ala  Glu  Glu  Gln  Val  Asn  Val  Pro  Phe  Leu  Pro
 15                       20                       25                       30

GAC  GAA  AGA  GCA  GTA  AAA  TGT  ATC  GGG  TGG  CAG  GAA  ACA  TGC  AAC  GGC    144
Asp  Glu  Arg  Ala  Val  Lys  Cys  Ile  Gly  Trp  Gln  Glu  Thr  Cys  Asn  Gly
                    35                       40                       45

AAC  TTG  CCC  TGC  TGC  AAT  GAG  TGC  GTC  ATG  TGC  GAA  TGC  AAC  ATT  ATG    192
Asn  Leu  Pro  Cys  Cys  Asn  Glu  Cys  Val  Met  Cys  Glu  Cys  Asn  Ile  Met
               50                       55                       60

GGT  CAA  AAC  TGC  AGA  TGC  AAC  CAT  CCC  AAA  GCA  ACT  AAC  GAA  TGC  GAG    240
Gly  Gln  Asn  Cys  Arg  Cys  Asn  His  Pro  Lys  Ala  Thr  Asn  Glu  Cys  Glu
          65                       70                       75

TCA  AGA  AGG  CGT  TGAAACAGCA  AAGAAATTAT  CTGTATGATT  TTTGGATTGA               292
Ser  Arg  Arg  Arg
          80
```

```
ATAAACGGGA GTAGATATGA                                                                                    312
```

( 2 ) INFORMATION FOR SEQ ID NO:29:

( i ) SEQUENCE CHARACTERISTICS:
        ( A ) LENGTH: 82 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Met Lys His Leu Ile Leu Ala Ser Ala Leu Ile Cys Ala Leu Val Val
 1               5                  10                  15

Cys Thr Ser Ala Glu Glu Gln Val Asn Val Pro Phe Leu Pro Asp Glu
            20                  25                  30

Arg Ala Val Lys Cys Ile Gly Trp Gln Glu Thr Cys Asn Gly Asn Leu
        35                  40                  45

Pro Cys Cys Asn Glu Cys Val Met Cys Glu Cys Asn Ile Met Gly Gln
    50                  55                  60

Asn Cys Arg Cys Asn His Pro Lys Ala Thr Asn Glu Cys Glu Ser Arg
65                  70                  75                  80

Arg Arg
```

( 2 ) INFORMATION FOR SEQ ID NO:30:

( i ) SEQUENCE CHARACTERISTICS:
        ( A ) LENGTH: 308 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 2..235

( x i ) SEQUENCE DESCRIPTION: SEQ ID NO:30:

```
C TTA GCA TCC GCC CTT ATC TGT GCA TTG GTC GTT TGC ACA TCT GCT         46
  Leu Ala Ser Ala Leu Ile Cys Ala Leu Val Val Cys Thr Ser Ala
   1               5                  10                  15

GAA GAG CAA GTG AAC GTG CCC TTT CTT CCT GAC GAA AGA GCA GTA AAA       94
Glu Glu Gln Val Asn Val Pro Phe Leu Pro Asp Glu Arg Ala Val Lys
                 20                  25                  30

TGT ATC GGG TGG CAG GAA ACA TGC AAC GGC AAC TTG CCC TGC TGC AAT      142
Cys Ile Gly Trp Gln Glu Thr Cys Asn Gly Asn Leu Pro Cys Cys Asn
             35                  40                  45

GAG TGC GTC ATG TGC GAA TGC AAC ATT ATG GGT CAA AAC TGC AGA TGC      190
Glu Cys Val Met Cys Glu Cys Asn Ile Met Gly Gln Asn Cys Arg Cys
         50                  55                  60

AAC CAT CCC AAA GCA ACT AAC GAA TGC GAG TCA AGA AGG CGT TGAAACAGCA   242
Asn His Pro Lys Ala Thr Asn Glu Cys Glu Ser Arg Arg Arg
     65                  70                  75

AAGAAATTAT CTGTATGATT TTTGGATTGA ATAAACGGGA GTAGATATGA CTCTGTTCGT    302

CTGTTA                                                               308
```

( 2 ) INFORMATION FOR SEQ ID NO:31:

( i ) SEQUENCE CHARACTERISTICS:
    ( A ) LENGTH: 77 amino acids
    ( B ) TYPE: amino acid
    ( D ) TOPOLOGY: linear ( i i ) MOLECULE TYPE: protein ( x i ) SEQUENCE DESCRIPTION: SEQ ID NO:31:

```
Leu Ala Ser Ala Leu Ile Cys Ala Leu Val Val Cys Thr Ser Ala Glu
 1               5                  10                  15

Glu Gln Val Asn Val Pro Phe Leu Pro Asp Glu Arg Ala Val Lys Cys
                20                  25                  30

Ile Gly Trp Gln Glu Thr Cys Asn Gly Asn Leu Pro Cys Cys Asn Glu
            35                  40                  45

Cys Val Met Cys Glu Cys Asn Ile Met Gly Gln Asn Cys Arg Cys Asn
        50                  55                  60

His Pro Lys Ala Thr Asn Glu Cys Glu Ser Arg Arg Arg
65                  70                  75
```

( 2 ) INFORMATION FOR SEQ ID NO:32:

( i ) SEQUENCE CHARACTERISTICS:
        ( A ) LENGTH: 314 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 3..242

( x i ) SEQUENCE DESCRIPTION: SEQ ID NO:32:

```
AG CAT TTG ATC TTA GCA TCC GCC CTT ATC TGT GCA TTG GTC GTT TGC        47
   His Leu Ile Leu Ala Ser Ala Leu Ile Cys Ala Leu Val Val Cys
    1               5                  10                  15

ACA TTT GCT GAA GAG CAA GTG AAC GTG CCC TTT CTT CCT GAC GAA AGA       95
Thr Phe Ala Glu Glu Gln Val Asn Val Pro Phe Leu Pro Asp Glu Arg
                    20                  25                  30

GAA GTA AAA TGT ATT GGG TGG CAG GAA TAT TGC CGC GGC AAC TTG CCC      143
Glu Val Lys Cys Ile Gly Trp Gln Glu Tyr Cys Arg Gly Asn Leu Pro
                35                  40                  45

TGC TGC GAT GAC TGC GTC ATG TGC GAA TGC AAC AAT ATG GGG CAA AAC      191
Cys Cys Asp Asp Cys Val Met Cys Glu Cys Asn Asn Met Gly Gln Asn
            50                  55                  60

TGC AGA TGC AAC CAC CCC AGA ATA ACT TCC GAG TGC GGG TCA AGG CGT      239
Cys Arg Cys Asn His Pro Arg Ile Thr Ser Glu Cys Gly Ser Arg Arg
        65                  70                  75

TGA AACAGCA AAGAAATTAT CTGTATGATT TTTGGATTGA ATAAACTGGA ATAGATATGA   299

CTCTGTTCGT CTGTT                                                     314
```

( 2 ) INFORMATION FOR SEQ ID NO:33:

( i ) SEQUENCE CHARACTERISTICS:
        ( A ) LENGTH: 79 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

| His | Leu | Ile | Leu | Ala | Ser | Ala | Leu | Ile | Cys | Ala | Leu | Val | Val | Cys | Thr |
|---|---|---|---|---|---|---|---|---|---|---|---|---|---|---|---|
| 1 | | | | 5 | | | | | 10 | | | | | 15 | |

| Phe | Ala | Glu | Glu | Gln | Val | Asn | Val | Pro | Phe | Leu | Pro | Asp | Glu | Arg | Glu |
|---|---|---|---|---|---|---|---|---|---|---|---|---|---|---|---|
| | | | 20 | | | | | 25 | | | | | 30 | | |

| Val | Lys | Cys | Ile | Gly | Trp | Gln | Glu | Tyr | Cys | Arg | Gly | Asn | Leu | Pro | Cys |
|---|---|---|---|---|---|---|---|---|---|---|---|---|---|---|---|
| | | 35 | | | | | 40 | | | | | 45 | | | |

| Cys | Asp | Asp | Cys | Val | Met | Cys | Glu | Cys | Asn | Asn | Met | Gly | Gln | Asn | Cys |
|---|---|---|---|---|---|---|---|---|---|---|---|---|---|---|---|
| | 50 | | | | | 55 | | | | | 60 | | | | |

| Arg | Cys | Asn | His | Pro | Arg | Ile | Thr | Ser | Glu | Cys | Gly | Ser | Arg | Arg |
|---|---|---|---|---|---|---|---|---|---|---|---|---|---|---|
| 65 | | | | | 70 | | | | | 75 | | | | |

( 2 ) INFORMATION FOR SEQ ID NO:34:

( i ) SEQUENCE CHARACTERISTICS:
        ( A ) LENGTH: 259 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..186

( x i ) SEQUENCE DESCRIPTION: SEQ ID NO:34:

| GAA | GAG | CAA | GTG | AAC | GTG | CCC | TTT | CTT | CCT | GAC | GAA | AGA | GCA | GTA | AAA | 48 |
|---|---|---|---|---|---|---|---|---|---|---|---|---|---|---|---|---|
| Glu | Glu | Gln | Val | Asn | Val | Pro | Phe | Leu | Pro | Asp | Glu | Arg | Ala | Val | Lys | |
| 1 | | | | 5 | | | | | 10 | | | | | 15 | | |

| TGT | ATC | GGG | TGG | CAG | GAA | ACA | TGC | AAC | GGC | CAG | CTC | CCC | TGC | TGC | GAT | 96 |
|---|---|---|---|---|---|---|---|---|---|---|---|---|---|---|---|---|
| Cys | Ile | Gly | Trp | Gln | Glu | Thr | Cys | Asn | Gly | Gln | Leu | Pro | Cys | Cys | Asp | |
| | | | 20 | | | | | 25 | | | | | 30 | | | |

| GGC | TGC | GTC | ATG | TGC | GAA | TGC | AAC | ATT | ATG | GGG | CAA | AAC | TGC | AGA | TGC | 144 |
|---|---|---|---|---|---|---|---|---|---|---|---|---|---|---|---|---|
| Gly | Cys | Val | Met | Cys | Glu | Cys | Asn | Ile | Met | Gly | Gln | Asn | Cys | Arg | Cys | |
| | | 35 | | | | | 40 | | | | | 45 | | | | |

| AAC | CAC | CCC | AAA | GCA | ACT | AAC | GAA | TGC | GAG | TCA | AGG | CGT | TGAAACAGCA | | | 193 |
|---|---|---|---|---|---|---|---|---|---|---|---|---|---|---|---|---|
| Asn | His | Pro | Lys | Ala | Thr | Asn | Glu | Cys | Glu | Ser | Arg | Arg | | | | |
| | 50 | | | | | 55 | | | | | 60 | | | | | |

AAGAAATTAT CTGTATGATT TTTGGATTG AATAAACGGG AGTAGATATG ACTCTGTTCG     253

TCTGTT     259

( 2 ) INFORMATION FOR SEQ ID NO:35:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

| Glu | Glu | Gln | Val | Asn | Val | Pro | Phe | Leu | Pro | Asp | Glu | Arg | Ala | Val | Lys |
|---|---|---|---|---|---|---|---|---|---|---|---|---|---|---|---|
| 1 | | | | 5 | | | | | 10 | | | | | 15 | |

| Cys | Ile | Gly | Trp | Gln | Glu | Thr | Cys | Asn | Gly | Gln | Leu | Pro | Cys | Cys | Asp |
|---|---|---|---|---|---|---|---|---|---|---|---|---|---|---|---|
| | | | 20 | | | | | 25 | | | | | 30 | | |

| Gly | Cys | Val | Met | Cys | Glu | Cys | Asn | Ile | Met | Gly | Gln | Asn | Cys | Arg | Cys |
|---|---|---|---|---|---|---|---|---|---|---|---|---|---|---|---|
| | | 35 | | | | | 40 | | | | | 45 | | | |

-continued

```
Asn His Pro Lys Ala Thr Asn Glu Cys Glu Ser Arg Arg
      50                  55                  60
```

(2) INFORMATION FOR SEQ ID NO:36:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:36:

```
CAATATATTA ATAGTTAAGA TATCAATTAT TATCAAATC                              39
```

INSECTICIDAL PLECTOXINS FROM *PLECTREURYS TRISTIS*

This is a continuation of application Ser. No. 08/163,602, filed Dec. 6, 1993, now abandoned, which is a continuation of application Ser. No. 08/058,051, filed May 3, 1993, now abandoned, which is a continuation of application Ser. No. 07/837,194, filed Feb. 11, 1992, now abandoned.

This invention relates to insecticidal plectoxins from the Primitive Hunting Spider, *Plectreurys tristis*, their nucleic acid and amino acid sequences, vectors containing the plectoxin genes, viruses containing the genes, and use of these plectoxins to control insects.

BACKGROUND OF THE INVENTION

In recent years, venoms of arachnids, in particular spiders and scorpions, have been investigated as a potential source of biologically active substances for use in various fields such as medicine and agriculture. Examples of such work include:

EP Patent Application, Publ. No. 208 523 A2: Glutamate Antagonists Isolated from New World Spiders *Aragiope trifasciata* and *Araneus gemma*.

EP Patent Application, Publ No. 156 540: Glutamate Receptor Inhibitor obtained from *Nephila clavata*.

Grishin et al., 1986. "Ion Channel Blocker from the Venom of *Argiope lobata*" *Biorg. Khim.* 12(8):1121–1124.

Usherwood et al., 1984. "Glutamate Channel Blockade by Venoms of *Argiope trifasciata* and *Araneus gemma*" *J. Physiol. Paris* 79:241–245.

Aramaki et al. 1986. "Glutamate Potential Suppressor from *Nephila clavata* and *Nephila maculata*" *Proc. Japan Acad.* 62, Ser B:359–362.

Usherwood et al., 1985. "Antagonism of Glutamate Receptor Channel Complexes by Spider Venom Polypeptides" *Neurotoxicology* (6(2):239–240.

Adams et al. 1986. "Synaptic Toxins from *Agelenopsis aptera*" *Insect Neurophysiology*, Borkovec et al., Eds. Humana Press, Clifton, N.J. 397–408.

The active principles isolated to date, however have usually been either complex polypeptides which are unsuited for medical and agricultural uses or have had activity levels too low to be of commercial interest.

DESCRIPTION OF THE INVENTION

It has now been found that certain polypeptides when isolated from the venom of the Primitive Hunting Spider, *Plectreurys tristis*, or polypeptides constructed to show substantial sequence homology to those isolated from the venom of *Plectreurys tristis*, are toxic, i.e. paralytic and/or lethal to insects, particularly of the order Lepidoptera, at surprisingly low concentrations. These polypeptides have been termed "Plectoxins".

The present invention, therefore, concerns plectoxins free from associated arachnoidal polypeptides which demonstrate toxicity towards insects. These polypeptides may be isolated from, or show substantial sequence homology to polypeptides isolated from the venom of *Plectreurys tristis*.

Figure 1:
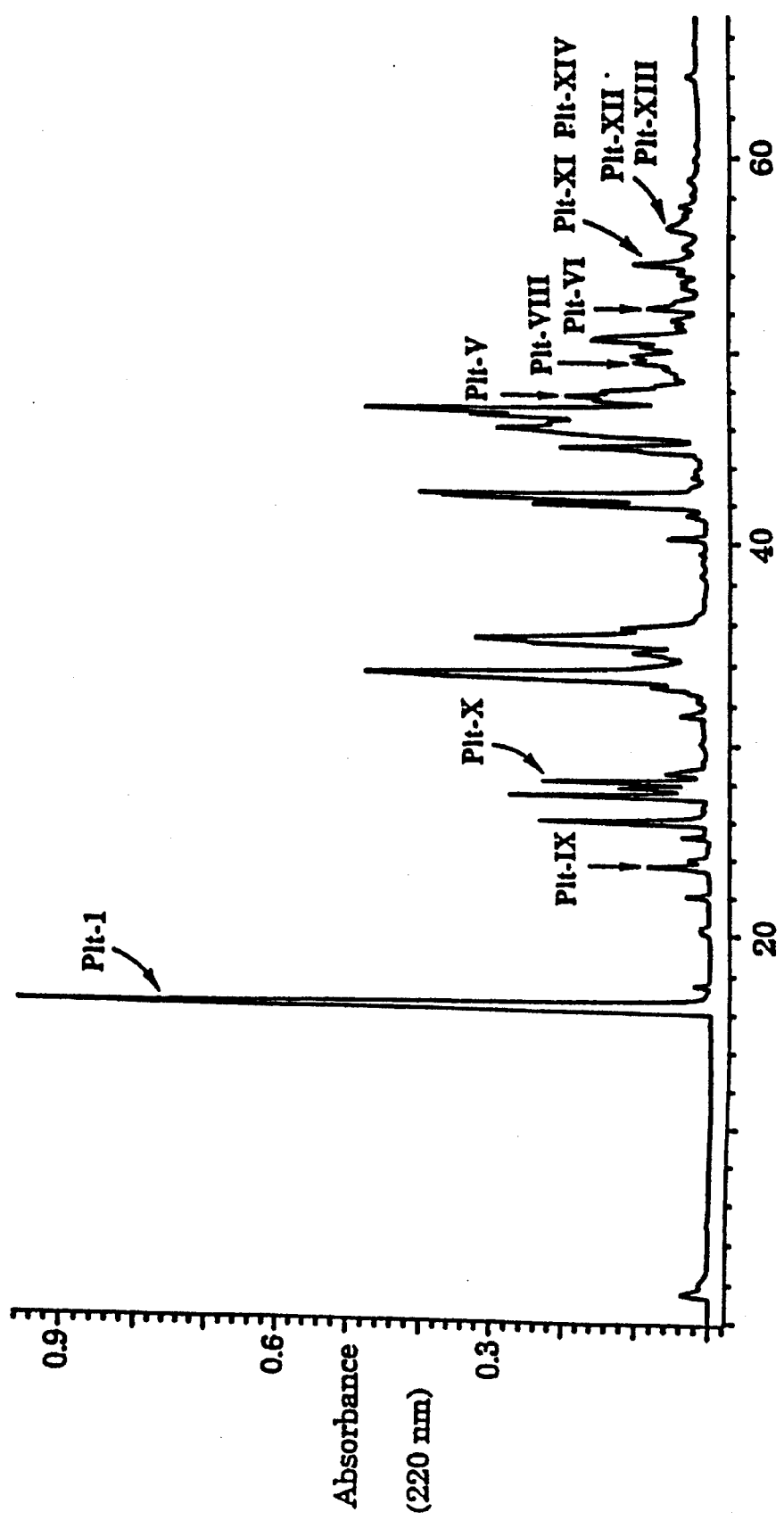
FIG. 1 shows the analytical separation of venom components by LC using a Vydac $C_{18}$ column (5 μm, 0.46×15 cm); linear gradient of 0–60% acetonitrile in a constant 0.1% TFA over 60 min; 1.5 ml/min; UV detection at 220 nm.
Figure 2:
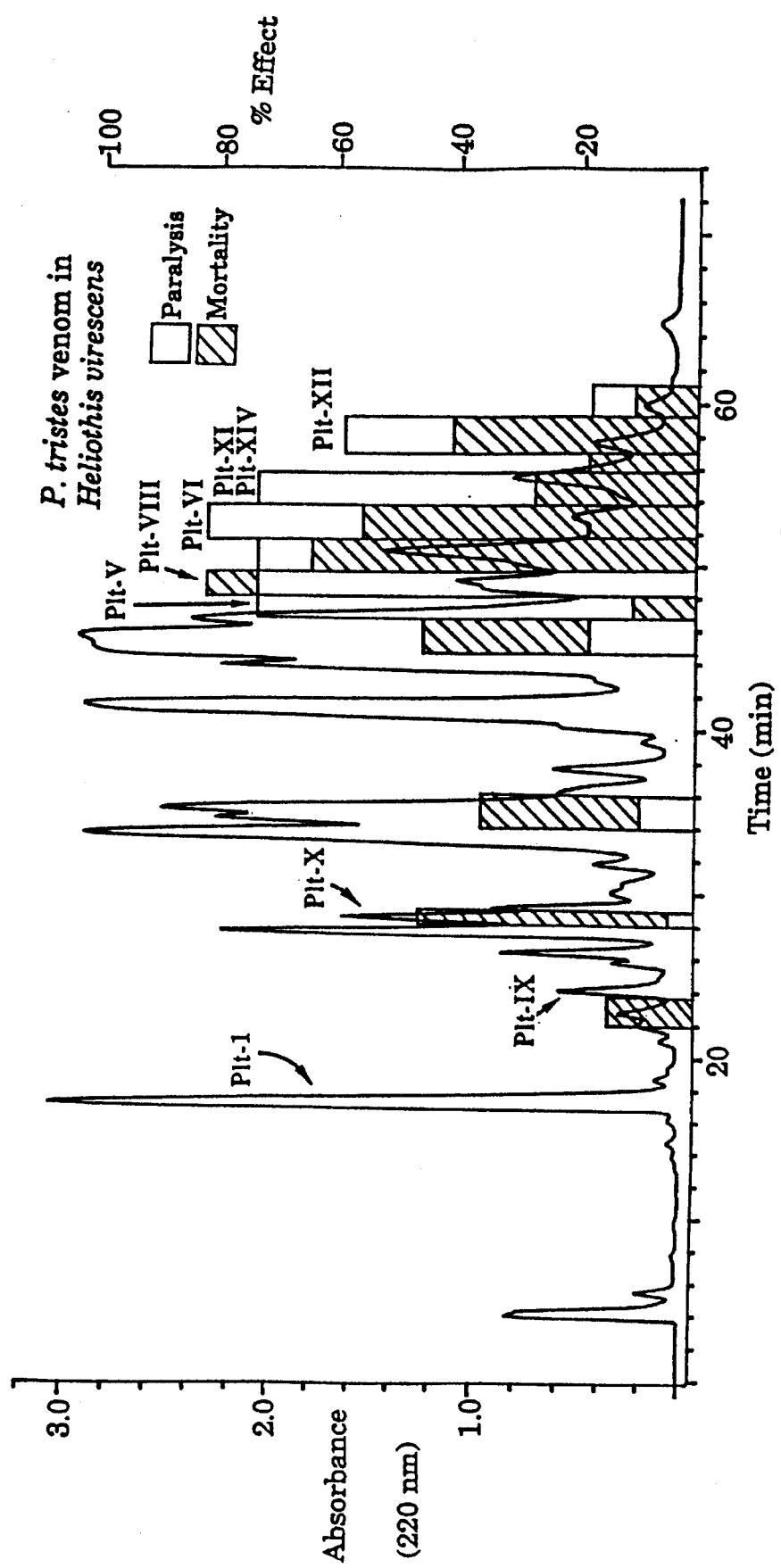
FIG. 2 shows venom components which are separated by LC (same conditions as in FIG. 1, except using an Aquapore ODS column, 1×22 cm, 4.5 ml/min) and their corresponding bioassay results in *Heliothis virescens* larvae. The solid line represents UV absorbance while a histogram of larvicidal activity (injection of fractions into larvae) is depicted by rectangular bars.
Figure 3A:
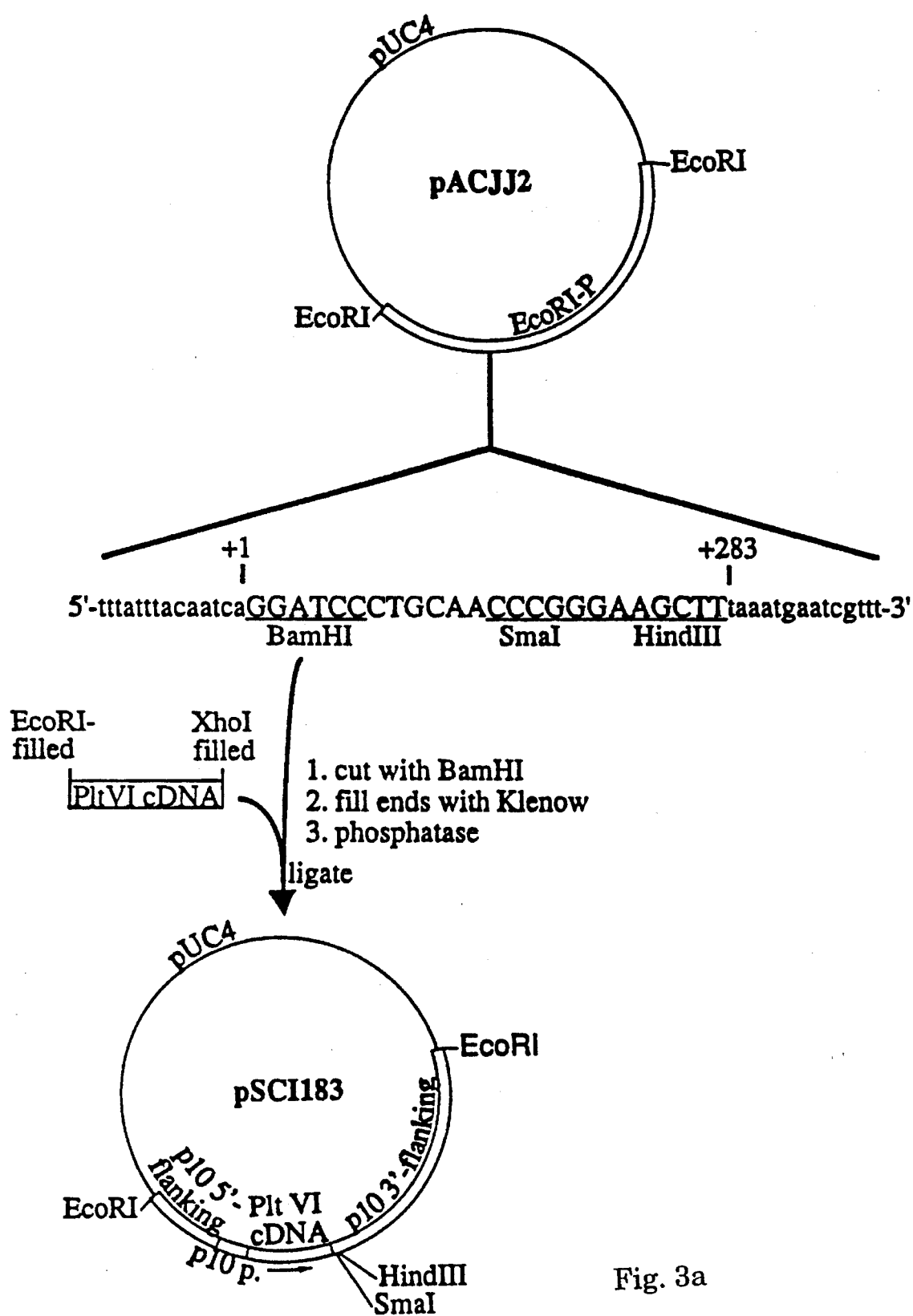
FIG. 3a illustrates the construction of plasmid pSCI183.
Figure 3B:
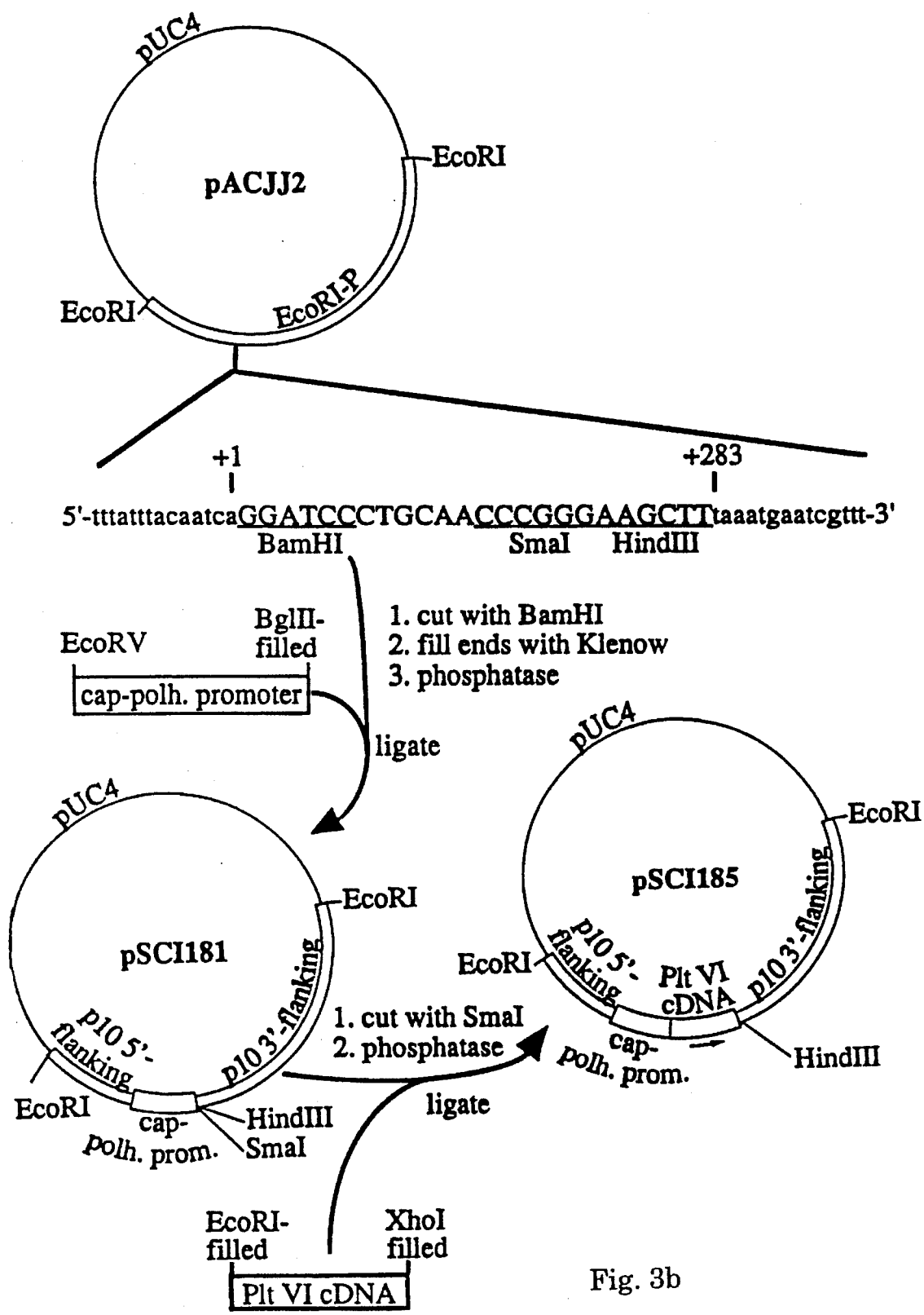
FIG. 3b illustrates the construction of plasmids pSCI181 and pSCI185.
Figure 4A:
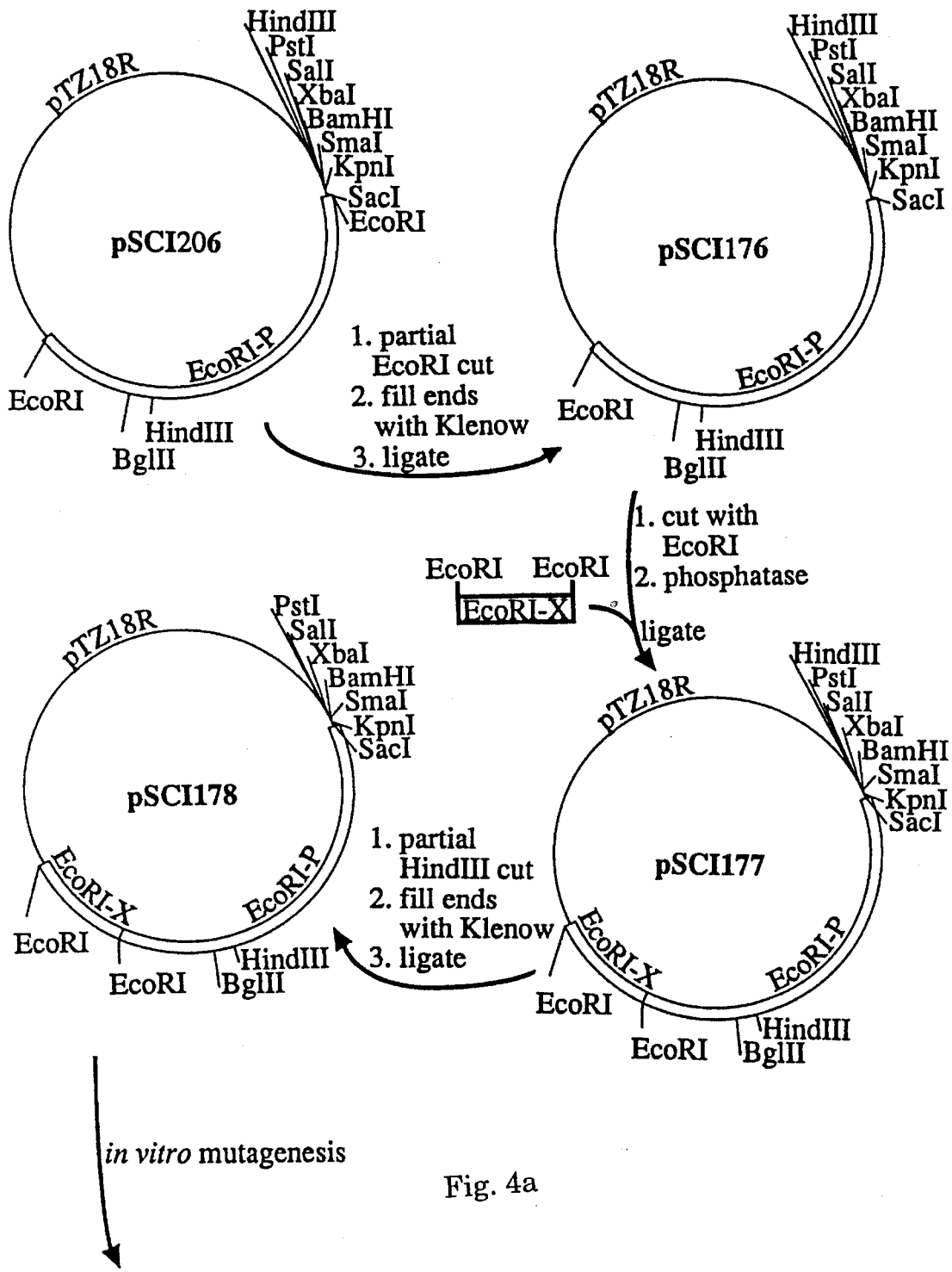
FIG. 4a illustrates the construction of plasmids pSCI176, pSCI177 and pSCI178.
Figure 4B:
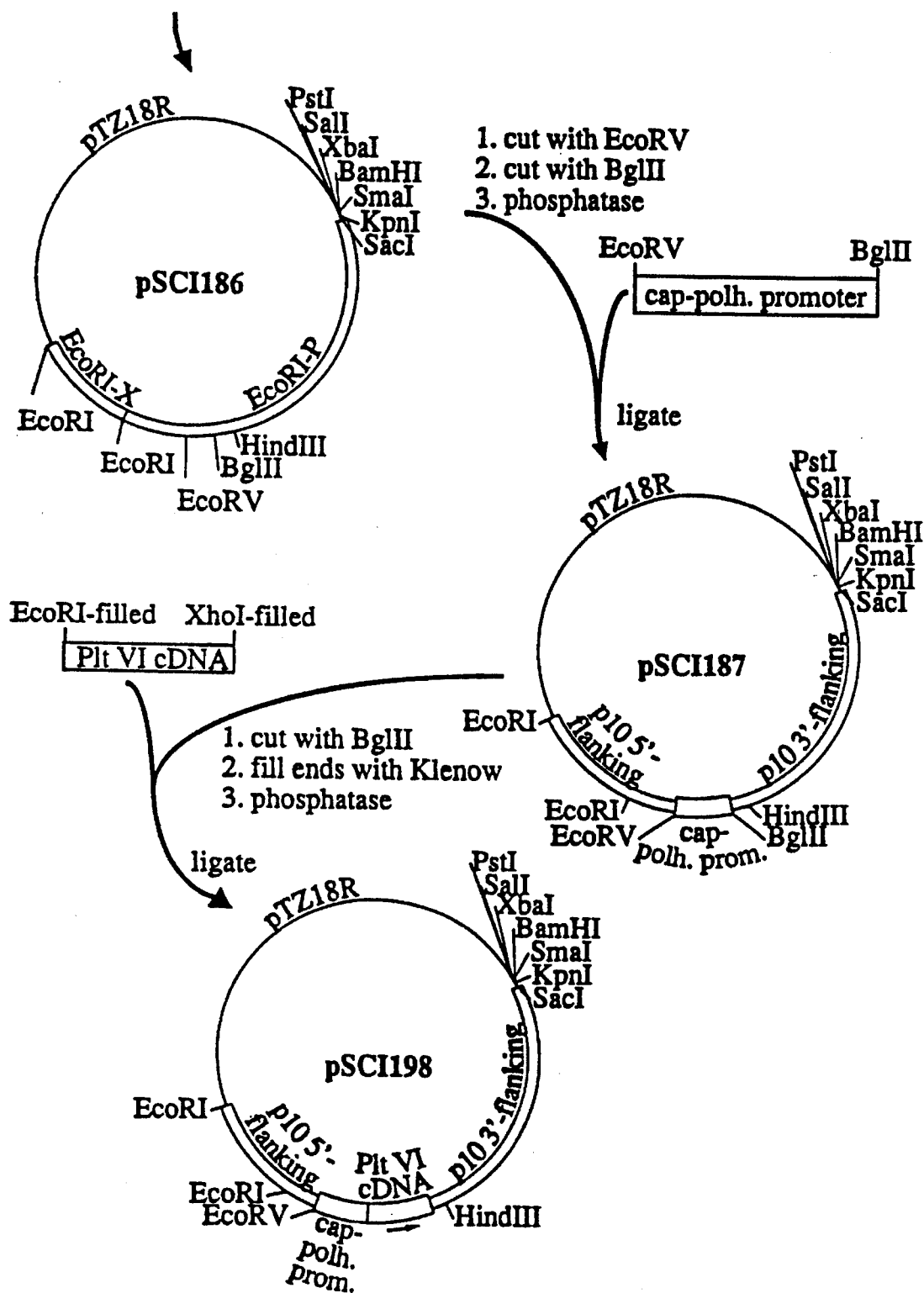
FIG. 4b illustrates the construction of plasmids pSCI186, pSCI187 and pSCI198 wherein pSCI186 is formed after exposed of pSCI178 of FIG. 4a to in vitro mutagenesis.

As used throughout the specification and claims, the following definitions are intended:

Associated arachnoidal polypeptides—insecticidal polypeptides naturally occurring in the venom of *P. tristis*.

Homologous polypeptides—polypeptides which are identical with respect to the number and positioning of the cysteine residues of one of the Plts of this invention, and substantially homologous with respect to the remainder of the amino acid sequences, such that they demonstrate insect toxicity.

Homologous nucleotide sequence—a sequence which will hybridize to the reference sequence under stringent hybridization conditions.

Stringent hybridization conditions—those in which hybridization is effected in a standard manner at 65° C. in 4× buffered saline (a.k.a. SSPE buffer) followed by merely washing at 52° C. in 0.2× SSPE, which will not affect true hybrids which have formed.

Analysis of the crude venom of *Plectreurys tristis* revealed the presence of some fifty distinct polypeptides which were insecticidally active. These were named Plt-I to Plt-L. Those exhibiting superior activity were further characterized and their amino acid sequences were determined. Thus one aspect of the present invention is directed to:

a polypeptide, free from associated arachnoidal polypeptides, comprising the following amino acid sequence (SEQ. ID. NO.: 1; Formula A):

$$AA_1\text{-}AA_2\text{-}Lys\text{-}Cys\text{-}AA_5\text{-}Gly\text{-}Trp\text{-}AA_8\text{-}AA_9\text{-}AA_{10}\text{-}Cys\text{-}AA_{12}\text{-}Gly\text{-}AA_{14}\text{-}AA_{15}\text{-}AA_{16}\text{-}Cys\text{-}Cys\text{-}AA_{19}\text{-}AA_{20}\text{-}Cys\text{-}Val\text{-}Met\text{-}AA_{24} \quad (A)$$

wherein $AA_1$ is Ala or Glu; $AA_2$ is Val or Leu; $AA_5$ is Ile or Gln; $AA_6$ is Gln or Val; $AA_9$ is Glu or Asp; $AA_{10}$ is Thr or Tyr; $AA_{12}$ is Asn or Arg; $AA_{14}$ is Asn or Lys; $AA_{15}$ is Leu or Val; $AA_{16}$ is Pro or Glu; $AA_{19}$ is Asn or Asp; $AA_{20}$ is Glu, Gly, or Asp; and $AA_{24}$ is Cys or Tyr; or a polypeptide comprising the sequence of Formula A and further comprising the following additional amino acids after $AA_{24}$ (SEQ. ID. NO.: 2; Formula B):

$$\text{-Glu-Cys-Asn-Ile-Met-Gly-Gln-Asn-Cys-Arg-Cys-Asn-His-Pro-}AA_{39}\text{-}AA_{40}\text{-Thr-}AA_{42} \quad (B)$$

wherein $AA_{39}$ is Lys or Arg; $AA_{40}$ is Ala, Met, or Ile; and $AA_{42}$ is Asn or Ser; or a polypeptide comprising the sequence of Formula B and further comprising an additional Glu after $AA_{42}$ (Formula C); or a polypeptide comprising the sequence of Formula C and further comprising the following additional amino acid sequence following the Glu at position 43 (Formula D):

Cys-AA$_{45}$  (D)

wherein AA$_{45}$ is Glu or Gly; or a polypeptide comprising the sequence of Formula D and further comprising a Ser after AA$_{45}$; (Formula E) or a polypeptide of the Formula F comprising the following amino acid sequence (SEQ. ID. NO.: 3):

Cys-Ala-Lys-His-Ser-Glu-Thr-Cys-Lys-Asn-Gly-Asn-Cys-Cys-Thr-
Cys-Thr-Gln-Tyr-Arg-Gly-Lys-Asp-Glu-Pro-Met-Ala-Cys-Arg-
Arg-Gly-Thr-His-Gly-Gln-Arg-Cys-Gln-Cys-Val-Met-Lys-Ile-
Met-Lys-His  (F)

or a polypeptide of the Formula G comprising the following amino acid sequence (SEQ. ID. NO.:4):

Gly-Cys-Lys-Gly-Phe-Leu-Val-Lys-Cys-Asp-Ser-Asn-Ser-Glu-Cys-
Cys-Lys-Thr-Ala-Ile-Val-Lys-Gly-Lys-Lys-Lys-Gln-Leu-Ser-
Cys-Leu-Cys-Gly-Ala-Trp-Gly-Ala-Gly-Cys-Ser-Cys-Ser-Phe-
Arg-Cys-Gly-Asn-Arg-Cys-OH  (G)

or a homologous peptide to any of the polypeptides of Formula A–G.

Preferred polypeptides are those of the Formula E' wherein AA$_1$ is Ala; AA$_2$ is Val; AA$_5$ is Ile; AA$_8$ is Gln; AA$_9$ is Glu; AA$_{10}$ is Thr; AA$_{12}$ is Asn; AA$_{14}$ is Asn or Lys; AA$_{15}$ is Leu; AA$_{16}$ is Pro; AA$_{19}$ is Asn or Asp; AA$_{20}$ is Glu or Gly; AA$_{24}$ is Cys; AA$_{39}$ is Lys or Arg; AA$_{40}$ is Ala or Met; AA$_{42}$ is Asn or Ser; and AA$_{45}$ is Glu or Gly.

As can be seen from the above formulae, the plectoxins of this invention are relatively small (molecular weight ca. 5,000 daltons). The most potent plectoxins have 10 half-cysteine residues, and presumably five interlinking disulfide bonds which produce a compact and relatively hydrophobic toxin. Since the carboxyl termini of at least three plectoxins are acidic, this appears to be a general feature of the plectoxins.

Preferred polypeptides of this invention are as follows:

Plt-VI: This is a particularly preferred polypeptide of this invention, characterized by being a peptide of the Formula E wherein AA$_1$=Ala, AA$_2$=Val, AA$_5$=Ile, AA$_8$=Gln, AA$_9$=Glu, AA$_{10}$=Thr, AA$_{12}$=Asn, AA$_{14}$=Asn, AA$_{15}$=Leu, AA$_{16}$=Pro, AA$_{19}$=Asn, AA$_{20}$=Glu, AA$_{24}$=Cys, AA$_{39}$=Lys, AA$_{40}$=Ala, AA$_{42}$=Asn, and AA$_{45}$=Glu.

Plt-V: a peptide of the Formula E wherein AA$_1$=Ala, AA$_2$=Val, AA$_5$=Ile, AA$_8$=Gln, AA$_9$=Glu, AA$_{10}$=Thr, AA$_{12}$=Asn, AA$_{14}$=Asn, AA$_{15}$=Leu, AA$_{16}$=Pro, AA$_{19}$=Asn, AA$_{20}$=Glu, AA$_{24}$=Cys, AA$_{39}$=Lys, AA$_{40}$=Ala, AA$_{42}$=Asn, and AA$_{45}$=Glu. Plt-VI and Plt-V differ in that reduction-alkylation of native Plt-V and Plt-VI produces chromatographically separable derivatives; while not wishing to be bound by theory, it appears that some post-translational modification at the C-terminus is responsible for the structural differences between the two plectoxins.

Plt-VIII: a peptide of the Formula E wherein AA$_1$=Ala, AA$_2$=Val, AA$_5$=Ile, AA$_8$=Gln, AA$_9$=Glu, AA$_{10}$=Thr, AA$_{12}$= Asn, AA$_{14}$=Lys, AA$_{15}$=Leu, AA$_{16}$=Pro, AA$_{19}$=Asp, AA$_{20}$=Gly, AA$_{24}$=Cys, AA$_{39}$=Lys, AA$_{40}$=Met, AA$_{42}$=Ser, and AA$_{45}$=Gly.

Plt-XI: a peptide of the Formula E wherein AA$_1$=Glu, AA$_2$=Val, AA$_5$=Ile, AA$_8$=Gln, AA$_9$=Glu, AA$_{10}$=Tyr, AA$_{12}$= Arg, AA$_{14}$=Asn, AA$_{15}$=Leu, AA$_{16}$=Pro, AA$_{19}$=Asp; AA$_{20}$= Asp, AA$_{24}$=Cys, AA$_{39}$=Arg, AA$_{40}$=Ile, AA$_{42}$=Ser, and AA$_{45}$=Gly.

Plt-XII: a peptide of the Formula D wherein AA$_1$=Ala, AA$_2$=Val, AA$_5$=Ile, AA$_8$=Gln, AA$_9$=Glu, AA$_{10}$=Thr, AA$_{12}$= Asn, AA$_{14}$=Asn, AA$_{15}$=Leu, AA$_{16}$=Pro, AA$_{19}$=Asn; AA$_{20}$= Glu, AA$_{24}$=Cys, AA$_{39}$=Lys, AA$_{40}$=Ala, AA$_{42}$=Asn, and AA$_{45}$=Glu.

Plt-XIII: a peptide of the Formula A wherein AA$_1$=Ala, AA$_2$=Leu, AA$_5$=Gln, AA$_8$=Val, AA$_9$=Asp, AA$_{10}$=Tyr; AA$_{12}$=Asn, AA$_{14}$=Asn, AA$_{15}$=Val, AA$_{16}$=Glu, AA$_{19}$=Asn, AA$_{20}$=Glu, and AA$_{24}$=Tyr.

Plt-XIV: a peptide of the Formula E wherein AA$_1$=Ala, AA$_2$=Val, AA$_5$=Ile, AA$_8$=Gln, AA$_9$=Glu, AA$_{10}$=Thr, AA$_{12}$= Asn, AA$_{14}$=Lys, AA$_{15}$=Leu, AA$_{16}$=Pro, AA$_{19}$=Asp, AA$_{20}$= Gly, AA$_{24}$=Cys, AA$_{39}$=Lys, AA$_{40}$=Ala, AA$_{42}$=Ser, and AA$_{45}$=Glu.

To determine their amino acid composition and precise amino acid sequence, the purified plectoxins were reduced, and carboxymethylated ([$^3$H]RCM). The individual [$^3$H] RCM polypeptide fractions were then proteolytically digested using various enzymes and the fragments produced were subjected to sequence analysis, amino acid composition analysis and COOH-terminus characterization using conventional techniques. Positions containing half-cysteine residues are verified by counting $^3$H from carboxymethyl moieties. The C-termini of Plt-V, Plt-VI, and Plt-X are free acids as determined by comparing C-terminal fragments with synthetic peptide fragments. Amino acid compositions of various Plts (native, RCM, and RCAM) and compositions for enzymatic fragments are given in the Examples, below.

A summary of the sequences of various polypeptides included in this invention is given in TABLE 1, below. The homology between the preferred polypeptides is apparent.

TABLE 1

| SEQ. NO. | PLT | | | | | |
|---|---|---|---|---|---|---|
| SEQ. ID. NO.:5 | V | AVKCIGWQET | CNGNLPCCNE | CVMCECNIMG | QNCRCNHPKA | TNECES-OH |
| SEQ. ID. NO.:5 | VI | AVKCIGWQET | CNGNLPCCNE | CVMCECNIMG | QNCRCNHPKA | TNECES-OH |
| SEQ. ID. NO.:6 | VIII | AVKCIGWQET | CNGKLPCCDG | CVMCECNIMG | QNCRCNHPKM | TSECGS |
| SEQ. ID. NO.:7 | XI | EVKCIGWQEY | CRGNLPCCDD | CVMCECNIMG | QNCRCNHPRI | TSECGS |
| SEQ. ID. NO.:8 | XII | AVKCIGWQET | CNGNLPCCNE | CVMCECNIMG | QNCRCNHPKA | TNECE |
| SEQ. ID. NO.:9 | XIII | ALKCQGWVDY | CNGNVECCNE | CVMY | | |
| SEQ. ID. NO.:10 | XIV | AVKCIGWQET | CNGKLPCCDG | CVMCECNIMG | QNCRCNHPKA | TSECES |
| SEQ. ID. NO.:3 | IX | CAKHSETCKN | GNCCTCTQYR | GKDEPMACRR | GTHGQRCQCV | MKIMKH |
| SEQ. ID. NO.:4 | X | GCKGFLVKCD | SNSECCKTAI | VKGKKKQLSC | LCGAWGAGCS | CSFRCGNRC-OH |

The preferred polypeptides of this invention bear remarkable homology, and, in particular with respect to the conservation of the number and positioning of the cysteine residues. It is believed that, because of their role in the formation of tertiary structures, the number and positioning of the cysteine in these insecticidally active polypeptides is of particular importance. Each of the above plectoxins demonstrates insect toxicity, i.e. paralysis and/or lethality and it is believed that minor substitutions in the polypeptide sequences of these plectoxins will not be detrimental to this activity, so that polypeptide sequences which are identical with respect to the number and positioning of the cysteine residues and substantially homologous with respect to the remainder of the amino acid sequences can also be expected to demonstrate insect toxicity. Such homologous polypeptides are also an aspect of this invention.

The polypeptides of this invention may be prepared by a variety of techniques. They may, for example, be isolated from the crude venom of *P. tristis* using purification techniques, such as those presented in the Examples. Alternatively, with knowledge of the amino acid sequence of the polypeptides, synthetic construction, using conventional protein synthesis techniques may be employed.

A further technique which may advantageously employed in the production of polypeptides of this invention involves the construction, by conventional methods, of a DNA sequence which, upon expression, encodes a polypeptide according to this invention. Such DNA sequence may then be inserted into an appropriate vector, either alone or in combination with other homologous or heterologous DNA sequences whose function maybe to control the expression of the polypeptide-encoding DNA sequence of interest or may result in, for example, a fusion protein, enhancing or extending the activity of the plectoxin DNA expression product therefrom. Suitably employed as vectors are plasmids, phages, and viruses, the use of which for such purpose is common knowledge to the ordinary artisan. Cells in which a vector containing such plectoxin DNA may be expressed, include, for example, prokaryotic cells such as *E. coli*, and *Bacillus spp.*, or eukaryotic cells such as yeast cells or insect cells.

A preferred method for producing the plectoxin polypeptides directly as a toxic product such that no work-up towards isolation, purification, and formulation of an expression product is required is by employing an insect specific virus (baculovirus) as a vector. A gene encoding the desired polypeptide plectoxin is inserted into the baculovirus DNA, and is under the control of a baculovirus promoter. After the recombinant hybrid baculovirus DNA is ingested by the insect, the virus multiplies inside the insect and the plectoxin is expressed (produced) in an amount sufficient to enhance the insecticidal effect on the insect. Such a recombinantly modified baculovirus DNA may also be used as a vector for the introduction of the spider plectoxin producing gene into cells, particularly insect cells, to provide further systems for the production of plectoxins.

A number of baculoviruses are suitable for use as vectors, and are known in the art, such as the nuclear polyhedrosis virus from *Autographa californica, Heliothis virescens*, and *Bombyx mori*. Suitable techniques are described, for example in European Patent Application 0175 852 and U.S. Pat. No. 4,745,051, both of which are hereby incorporated by reference.

Thus another aspect of this invention are nucleic acids sequences (RNAs and DNAs) comprising those which encode polypeptides of the Formulas A–E, and nucleic acid sequences which are homologous nucleic acids. The nucleic acid sequences of this invention may also include sequences which are not expressed in the final polypeptide product, such as signal sequences, termination sequences, and the like.

A further aspect of this invention, therefore involves the cloning and genetic engineering of the various plectotoxins, and in particular Plt-VI.

Starting with 25 cephalothoraces (approximately 1 g), approximately 8 µg of poly A+ mRNA was obtained using the procedures detailed in the Example 3. Degenerate oligonucleotide primers corresponding to two regions of the nucleotide sequence obtained by reverse translation of the mature Plt-VI peptide were synthesized and used for PCR amplification from *P. tristis* mRNA. DNA fragments with the expected size of approximately 130 bp were produced in the PCR reaction. The DNA fragments were gel purified, cloned into pTZ18R, and four clones were sequenced. One of these clones contained a reading frame that matched a portion of the amino acid sequence of mature Plt-VI plectoxin. A nondegenerate primer designed to match a region from within the amplified sequence was end-labelled with $^{32}$P and used to screen a λZAPII cDNA library made from *P. tristis* cephalothorax mRNA. 73 positive plaques were detected in a library screening of approximately $1\times10^6$ plaques.

After plaque purification and in vivo excision of the cDNA containing pBluescript SK- plasmids from the λZAPII clones, the cDNA inserts of 9 clones were subjected to DNA sequence analysis. In order to determine the expected size of a full length cDNA, a primer extension reaction was performed with *P. tristis* cephalothorax mRNA. Two major bands and several minor bands (approximately 20–30 bases larger than the major bands) were detected. Analysis of the largest cDNA clone, pSCI263, revealed that it was several bases longer at the N-terminus than predicted for full length cDNA based on the sizes of the major primer extension products, suggesting that it may be derived from a mRNA which initiates at one of the positions indicated by the minor bands. A long open reading frame of 246 nucleotides, predicting an amino acid sequence of 82 residues, was found within the cDNA sequence. The amino acid sequence determined for the mature form of plectoxin Plt-VI was present within this open reading frame, beginning at amino acid position 34, and ending at position 79. This is followed by three C-terminal arginines which are processed off of the mature form, presumably by a carboxypeptidase-B-like enzyme. The first 20 amino acids conform to a consensus signal sequence. Signal sequence cleavage is predicted to leave a 13 amino acid pro-region ending in a single arginine, which must be processed off by an endoprotease to release the mature peptide.

The remaining eight cDNA clones were much shorter than full length. All nine clones contained putative polyadenylation signals (AATAAA) near the 3' terminus. In six of the nine clones, the poly(A)+ tail is positioned 20 nucleotides downstream from the beginning of the polyadenylation signal, and in the remaining 3 clones, the poly(A)+ tail is positioned an additional 3 to 21 bases further downstream.

Seven of the nine clones contain reading frames with sections corresponding to the full length of mature Plt-VI (TABLE 10) (SEQ. ID. NO.:5). In these seven clones, three arginine codons follow the carboxy terminus of the mature protein. Translational initiation very likely occurs at the ATG underlined in TABLE 10, since a) this is the first methionine codon encountered in the nearly full length cDNA; b) the codon for this methionine is found in the sequence AACCATGA, which conforms to the ribosome initiation site consensus sequence determined by Kozak, 1989. *J. Cell Biol.* 108:229–241, and c) there is a translational stop sequence, TGA, in frame with the Plt-VI open reading frame beginning 21 bp upstream from this methionine codon. Thus the Plt-VI protein is predicted to be synthesized as a prepro-protein in which the 33 N-terminal and the 3 C-terminal amino acids are processed off to generate the mature form as shown in TABLE 9. The additional 33 amino acids at the N-terminus contain a predicted signal sequence with a cleavage site following the alanine at position 20 (von Heijne, G. 1986. *Nucl. Acids Res.* 14:4683–4690.), leaving a 13 amino acid pro-sequence which would be cleaved following the single arginine at position 33. The prepro-protein and proprotein forms of plectotoxins in general and Plt-VI in particular are thus another aspect of this invention, as are nucleic acid sequences which encode these.

The clone pSCI265 has a reading frame with a section corresponding to the 46 amino acid sequence determined for Plt-XI. The clone pSCI272 has a reading frame with a section identical to Plt-VIII, except for a glutamine to lysine change at $AA_{47}$. Both of these clones have only two C-terminal arginine codons, compared to the three C-terminal arginine codons found in Plt-VI cDNAs.

Because of the very high level of paralytic activity that Plt-VI plectoxin elicits upon injection of a number of different insects, cDNAs encoding prepro-Plt-VI plectoxin may be cloned in an insect baculovirus. Upon expression in the insect, there will be a quicker cessation of feeding than occurs after infection with wild type baculoviruses. Insect baculoviruses occur in two forms, occluded viruses, which are responsible for the spread of viruses between insects, and nonoccluded or budded viruses which are responsible for the cell to cell spread of viruses within an infected insect. Infection of insects per os normally requires the occluded form of the virus. Thus a further aspect of this invention is a recombinant virus containing a gene encoding a plectoxin or pre-plectoxin or prepro-plectoxin of this invention inserted at a locus such that occlusion body formation is not disrupted. One such locus is the p10 locus.

Polypeptides isolated from or those showing substantial homology to those isolated from the venom of *Plectreurys tristis* are useful as insecticidal agents. In particular, they are useful insecticidal agents against insects of the order Lepidoptera, for example, *Heliothis virescens, Autographa californica*, and the insects of the genus Spodoptera. Both the purified plectoxin and viruses transformed to produce the plectoxin are assayed for bioactivity on larvae including: tobacco hornworms (*Manduca sexta*), tobacco budworms (*Heliothis virescens*) and beet armyworm (*Spodoptera exigua*). Toxicity is demonstrated by the ability of the polypeptides to cause paralysis and/or death of the test larvae.

The present invention also provides the use of polypeptides isolated from, or polypeptides showing substantial sequence homology to those isolated from *Plectreurys tristis* as insecticides. For use as insecticides, the recombinant viruses which produce polypeptides of the invention may be combined with suitable carrier substances such as those typically found in insect control formulations, such as adjuvants, diluents, modifiers or conditioning agents. The formulations may be in the form of solutions, emulsions, dispersions, powders, dusts, granules and the like. It may be advantageous to include a surface active agent such as DMSO in the formulation so that the plectoxin passes directly through the cuticle of the insect and avoids the digestive enzymes which might affect its activity.

These compositions are advantageously applied to the insect or its locale in an amount suitable to control the target insects. "Control", as used herein, means the induction of paralysis, mortality, or cessation of eating. Dosages of the composition of the invention will depend on numerous factors, including the pest to be controlled and the climatic conditions, but will generally be in the range of 0.5 to 100 kg/hectare, preferably 10–50 kg/hectare.

The following non-limiting Examples are presented to better illustrate the invention.

EXAMPLE 1

Purification of Spider Venom

Venom from *P.tristis* is obtained from Spider Pharm, Black Canyon City, Ariz. Crude venom (approximately 200 μl per injection) is fractionated by reversed-phase liquid chromatography (LC) using the following conditions: a Perkin Elmer Model 410 Bio solvent delivery system; 5 ml injection loop; Hewlett Packard Model 1040M diode array detector at 220 and 280 nm; Aquapore ODS column, 22×1 cm (Brownlee Labs, Santa Clara, Calif.); 4.5 ml/min; acetonitrile (MeCN) in a constant 0.1% trifluoroacetic acid, 0% MeCN for 5 min, then linear gradient of 0 to 60% MeCN over 55 min. Similar fractions from several runs are combined and portions are removed for bioassays. Aliquots of individual fractions are added to 1.5 ml polypropylene tubes containing 150 μg bovine serum albumin and are evaporated to dryness in a Speed Vac Concentrator (Savant). Physiological saline (35 μl) is added and 3 μl aliquots are injected into *H. virescens* larvae to determine bioactivity.

On the basis of bioactivity, certain UV-active zones are selected for further purification by reversed-phase liquid chromatography and bioassay. Thus, Plt-V, Plt-VI and Plt-VIII are further purified using Vydac columns (0.46×15 cm, 300 Angstrom, $C_4$ or $C_{18}$; Separations Group, Hesperia, Calif.) and either MeCN or 1-propanol in a constant 0.1% TFA with linear gradients. Plt-V is further purified as follows with a $C_4$ column: 20% MeCN for 5 min; gradient 20–45% MeCN over 60 min; 1.5 ml/min; 15% 1-propanol for 5 min. gradient 20–45% MeCN over 60 min, 1.5 ml/min; 15% 1-propanol for five min, 15–40% 1-propanol over 60 min, 0.8 ml/min. Plt-VI is further purified with a $C_4$ column: 30% MeCN for 5 min, 30–50% MeCN over 60 min, 1.5 ml/min; 20% 1-propanol for 5 min, 20–45% 1-propanol over 60 min, 0.8 ml/min. Plt-VIII is further purified with a $C_{18}$ column: 25% MeCN for 5 min, 25–55% MeCN over 55 min, 1.5 ml/min. Other plectotoxins are purified similarly.

Analysis Purified Plt-V, Plt-VI, and Plt-VIII are reduced and alkylated as follows. 1–5 nmol of the plectoxin is dissolved in 300 μl 6M guanidine hydrochloride (0.5M Tris-Hcl, pH 8.5). Peptides are reduced in 0.8 μmol dithiothreitol (DTT) at 37° C. for 4 hours under argon. 2.3 μmol of either tritiated iodoacetic acid or nonradiolabeled iodoacetamide is added and the sample is allowed to stand at room temperature for 10 min. An additional 2.7 μmol nonradiolabeled iodoacetic acid (or iodoacetamide) is added. After another 10 min, 4.1 μmol DTT is added for repeated reduction for 1 hour at 37° C. A final addition of 13.5 μmol iodoacetic acid or iodoacetamide completes the alkylation. The reduced, carboxymethylated (RCM) and carboxamidomethylated (RCAM) peptides are purified by LC using a Vydac $C_{18}$ column and a gradient of MeCN in 0.1% TFA: 25% MeCN for 5 min, and 25–55% MeCN over 55 min. The results are presented in TABLE 2.

TABLE 2

Amino acid sequences of plectoxins showing fragments from enzyme cleavage: Tr, trypsin; G, endopeptidase Glu-C; Th, thermolysin; Ch, α-chymotrypsin; As, Asp-N.

```
                    1         10        20        30        40
Plt-V               A V K C I G W Q E T C N G N L P C C N E C V M C E C N I M G Q N C R C N H P K A T N E C E S-OH
(SEQ. ID. NO. 5)    |- Tr-1 -||------------------ Tr-2 -------------------||- Tr-3 -||- Tr-4 -|
                    |------ G-1 -------||------ G-2 ------||- G-3 -||------------ G-4 ------------|

1         10        20        30        40
Plt-VI              A V K C I G W Q E T C N G N L P C C N E C V M C E C N I M G Q N C R C N H P K A T N E C E S-OH
(SEQ. ID. NO. 5)    |- Tr-5 -||------------------ Tr-6 -------------------||- Tr-7 -||- Tr-8 -|
                    |- Th-1 -||------------------ Th-2 -----------------||-------- Th-3 --------|

1         10        20        30        40
Plt-VIII            A V K C I G W Q E T C N G K L P C C D G C V M C E C N I M G Q N C R C N H P K M T S E C G S
(SEQ. ID. NO. 6)    |- Tr-9 -||------------------ Tr-10 ------------------||- Tr-11 -||- Tr-12 -|

1         10        20        30        40
Plt-IX              C A K H S E T C K N G N C C T C T Q Y R G K D E P M A C R R G T H G Q R C Q C V M K I M K H
(SEQ. ID. NO. 3)

1         10        20        30        40
Plt-X               G C K G F L V K C D S N S E C C K T A I V K G K K K Q L S C L C G A W G A G C S C S F R C G N R C-OH
(SEQ. ID. NO. 4)    |------------------------------- Ch-1 -------------------------------||--- Ch-2 ---|
                    |- Ch-3 -|
                    |------------------------ Ch-4 ------------------------|     |--- Ch-5 ---|

1         10        20        30        40
Plt-XI              E V K C I G W Q E Y C R G N L P C C D D C V M C E C N I M G Q N C R C N H P R I T S E C G S
(SEQ. ID. NO. 7)    |--- As-1 ---||--- As-2 ---||-------------------- As-3 --------------------|
                    |---------- As-4 ----------||-- As-5 --||------------ As-6 ------------|
                                                                              |--- As-7 ---|
                    |- Tr-13 -||-- Tr-14 --||---------------- Tr-15 ----------------||- Tr-16 -|
                              |--------------------------- Tr-17 ---------------------------|
```

Derivatized peptides (RCM and RCAM) are cleaved with enzymes to produce fragments which would aid in structural assignments. Typically 1–2 nmol peptides in LC solvent are added to 1.5 ml polypropylene tubes. After concentration to 100–150 µl, 300 µl 0.1M $NH_4HCO_3$ (pH 8) is added. Samples are concentrated to approximately 300 µl. The following conditions are used for individual enzymes: trypsin (0.5 µg), RCM peptide, 37° C., 4 hrs; thermolysin (0.25 µg), RCM peptide, 5 mM in $CaCl_2$, 37° C., 4 hrs; endopeptidase Glu-C (1 µg), RCAM peptide, 1 mM in EDTA, room temperature, 20 hrs. Samples are acidified with 1% TFA and then concentrated to approximately 200 µl prior to LC analysis using a Vydac $C_{18}$ column, MeCN in a constant 0.1% TFA, 0% MeCN for 5 min, gradient 0 to 60% MeCN over 80 min, 0.5 ml/min.

Plectotoxins (native, RCM and RCAM) and fragments are sequenced using a pulsed liquid-phase protein sequencer (Applied Biosystems Model 477A with phenylthiohydantoin analyzer, Model 120A, on line). Individual PTH amino acids are collected for quantification of $^3H$ from alkylated half-cysteine residues by liquid scintillation counting (Packard Model 4430). Peptides are also hydrolyzed by vapor in vacuo (6M HCl/1% phenol, 110° C. for 20 h) for amino acid analysis. After conversion to phenylthiocarbamoyl derivatives, amino acids are analyzed by LC (Ultrashpere ODS column, 0.46×15 cm, Altex).

Heptapeptides ($ATNECES-NH_2$ and ATNECES-OH SEQ. ID. NO.:11) are synthesized for analysis of the carboxyl terminus from Plt-V and Plt-VI. Crude peptides are reduced, carboxymethylated (as above) and purified by LC. Peptide sequencing confirms the structures of these peptides which are compared by LC to the corresponding tryptic fragments from Plt-V and Plt-VI. Results are presented in Tables 3–6a, below.

TABLE 3

Amino acid compositions of plectoxins

| Amino acid | Plt-V Native | Plt-V RCM[a] | Plt-V RCAM[b] | Plt-VI Native | Plt-VI RCAM | Plt-VIII Native | Plt-VIII RCAM |
|---|---|---|---|---|---|---|---|
| ½ Cys |  | 10.8(10)[c] | 9.0(10) |  | 9.4(10) |  | 9.4(10) |
| Cys-OH[d] | [e](10) |  |  | 9.9(10) |  | 10.1(10) |  |
| Asx | 7.0 (7) | 6.9 (7) | 6.9 (7) | 6.6 (7) | 6.4 (7) | 4.9 (5) | 4.5 (5) |
| Glx | 7.8 (7) | 7.1 (7) | 6.8 (7) | 6.7 (7) | 6.4 (7) | 4.6 (5) | 4.4 (5) |
| Ser | 1.5 (1) | 1.3 (1) | 1.2 (1) | 1.8 (1) | 1.1 (1) | 2.0 (2) | 1.9 (2) |
| Gly | 3.3 (3) | 3.2 (3) | 3.0 (3) | 3.8 (3) | 2.9 (3) | 4.9 (5) | 4.8 (5) |
| His | 1.0 (1) | 1.2 (1) | 1.1 (1) | 1.0 (1) | 1.1 (1) | 1.0 (1) | 1.0 (1) |
| Thr | 2.0 (2) | 1.9 (2) | 1.9 (2) | 1.8 (2) | 1.9 (2) | 1.8 (2) | 1.9 (2) |
| Ala | 2.0 (2) | 2.4 (2) | 2.4 (2) | 2.2 (2) | 2.1 (2) | 1.3 (1) | 1.1 (1) |
| Arg | 1.4 (1) | 1.4 (1) | 1.3 (1) | 1.5 (1) | 1.2 (1) | 1.2 (1) | 1.1 (1) |
| Pro | 2.3 (2) | 2.0 (2) | 2.1 (2) | 2.0 (2) | 2.1 (2) | 2.1 (2) | 2.1 (2) |
| Tyr | 0.7 (0) | 0.1 (0) | 0.2 (0) | 0.2 (0) | 0.1 (0) | 0.0 (0) | 0.1 (0) |
| Val | 2.2 (2) | 2.0 (2) | 2.0 (2) | 2.0 (2) | 2.0 (2) | 1.9 (2) | 2.0 (2) |
| Met | 2.0 (2) | 2.2 (2) | 2.0 (2) | 1.9 (2) | 1.9 (2) | 2.7 (3) | 2.8 (3) |
| Ile | 1.8 (2) | 0.9 (2) | 2.0 (2) | 1.8 (2) | 1.9 (2) | 1.6 (2) | 1.7 (2) |
| Leu | 1.6 (1) | 1.4 (1) | 1.4 (1) | 1.5 (1) | 1.2 (1) | 1.1 (1) | 1.1 (1) |
| Phe | 0.4 (0) | 0.0 (0) | 0.3 (0) | 0.3 (0) | 0.1 (0) | 0.1 (0) | 0.0 (0) |
| Lys | 2.5 (2) | 2.3 (2) | 2.2 (2) | 2.4 (2) | 2.1 (2) | 3.2 (3) | 3.3 (3) |
| Trp[e] | (1) | (1) | (1) | (1) | (1) | (1) | (1) |

[a]Reduced, carboxymethylated (RCM)
[b]Reduced, carboxamidomethylated (RCAM).
[c]Number of residues determined from sequence analysis.
[d]Cysteic acid from oxidation with performic acid.
[e]Not determined.

TABLE 4

Amino acid compositions of Plt-IX, Plt-X, carboxymethyl derivatives (RCM), and α-chymotryptic (Ch) fragments

| | Plt-IX | | Plt-X | | | | | |
|---|---|---|---|---|---|---|---|---|
| | native | RCM[a] | RCM | Ch-1 | Ch-2 | Ch-3 | Ch-4 | Ch-5 |
| ½ Cys | (8)[b] | 7.4 (8) | 10.8 (10) | 9.3 (8) | 2.1 (2) | 1.0 (1) | 4.1 (4) | 0.9 (2) |
| Asx | 3.0 (3) | 2.7 (3) | 2.9 (3) | 2.2 (2) | 0.7 (1) | | 2.4 (2) | |
| Glx | 4.4 (5) | 3.9 (5) | 2.1 (2) | 2.1 (2) | 0.9 (1) | | 1.9 (2) | |
| Ser | 1.0 (1) | 1.0 (1) | 4.8 (5) | 4.9 (5) | | | 2.3 (2) | 1.8 (2) |
| Gly | 4.3 (4) | 4.2 (4) | 7.3 (7) | 6.5 (6) | | 2.3 (2) | 3.5 (3) | 2.2 (2) |
| His | 3.0 (3) | 2.6 (3) | 0.0 (0) | 0.1 (0) | | | 0.3 (0) | |
| Thr | 4.1 (4) | 4.0 (4) | 0.9 (1) | 0.9 (1) | | | 1.0 (1) | |
| Ala | 2.4 (2) | 2.3 (2) | 3.5 (3) | 3.5 (3) | | | 1.3 (1) | 1.1 (1) |
| Arg | 4.4 (4) | 4.1 (4) | 2.4 (2) | 0.1 (0) | 2.1 (2) | | 0.2 (0) | |
| Pro | 1.1 (1) | 1.1 (1) | 0.0 (0) | 0.0 (0) | | | 0.0 (0) | |
| Tyr | 1.0 (1) | 1.0 (1) | 0.0 (0) | 0.1 (0) | | | 0.0 (0) | |
| Val | 0.9 (1) | 1.0 (1) | 1.3 (2) | 1.2 (2) | | | 1.5 (2) | |
| Met | 2.8 (3) | 2.5 (3) | 0.1 (0) | 0.1 (0) | | | 0.0 (0) | |
| Ile | 0.8 (1) | 0.8 (1) | 0.6 (1) | 0.6 (1) | | | 0.7 (1) | |
| Leu | 0.2 (0) | 0.2 (0) | 3.4 (3) | 3.3 (3) | | | 2.0 (2) | 0.9 (1) |
| Phe | 0.0 (0) | 0.0 (0) | 2.2 (2) | 2.1 (2) | | 1.0 (1) | 1.1 (1) | |
| Lys | 5.4 (5) | 5.0 (5) | 7.8 (7) | 6.5 (7) | | 0.9 (1) | 6.6 (7) | |
| Trp[c] | (0) | (0) | (1) | (1) | | | (0) | |

[a]Reduced, carboxymethylated (RCM).
[b]Number of residues determined by sequence analysis.
[c]Not determined.

TABLE 5

Amino acid compositions of fragment peptides from Plt-V: Tr, trypsin; G, endopeptidase Glu-C

| | Tr-1 | Tr-2 | Tr-3 | Tr-4 | G-1 | G-2 | G-3 | G-4 |
|---|---|---|---|---|---|---|---|---|
| ½ Cys[a] | | 8.5 (8)[b] | 1.3 (1) | 0.7 (1) | 0.9 (1) | 2.9 (3) | 2.6 (2) | 3.2 (3) |
| Asx | | 4.6 (5) | 0.9 (1) | 1.3 (1) | | 2.6 (3) | | 2.7 (4) |
| Glx | | 4.8 (5) | | 1.8 (2) | 2.3 (2) | 0.9 (1) | 0.9 (1) | 2.1 (2) |
| Ser | | | | 0.9 (1) | | | | |
| Gly | | 2.9 (3) | | | 1.8 (1) | 1.0 (1) | | 1.3 (1) |
| His | | | 1.4 (1) | | | | | 0.7 (1) |
| Thr | | 0.9 (1) | | 1.3 (1) | | 0.8 (1) | | 0.9 (1) |
| Ala | 1.2 (1) | | | 1.0 (1) | 1.3 (1) | | | 1.0 (1) |
| Arg | | 1.3 (1) | | | | | | 1.2 (1) |
| Pro | | 1.1 (1) | 1.1 (1) | | | 0.9 (1) | | |
| Tyr | | | | | | | | |
| Val | 1.0 (1) | 1.1 (1) | | | 1.0 (1) | | 1.0 (1) | 1.1 (1) |
| Met | | 2.2 (2) | | | | | 1.0 (1) | 1.1 (1) |
| Ile | | 2.0 (2) | | | 1.0 (1) | | | 1.0 (1) |
| Leu | | 1.2 (1) | | | | 1.0 (1) | | |
| Phe | | | | | | | | |
| Lys | 0.9 (1) | | 1.0 (1) | | 1.0 (1) | 0.8 (1) | | |
| Trp[c] | | (1) | | | (1) | | | |

[a]Determined from carboxymethylated (Tr) and carboxamidomethylated (G) fragments.
[b]Number of residues determined from sequence analysis.
[c]Not determined.

TABLE 6

Amino acid compositions of tryptic peptides from Plt-VI and Plt-VIII

| | Plt-VI | | | | Plt-VIII | | | |
|---|---|---|---|---|---|---|---|---|
| | Tr-5 | Tr-6 | Tr-7 | Tr-8 | Tr-9 | Tr-10 | Tr-11 | Tr-12 |
| ½ Cys[a] | | 7.9 (8)[b] | 1.0 (1) | 0.5 (1) | | 7.6 (8) | 1.1 (1) | 1.0 (1) |
| Asx | | 4.8 (5) | 1.0 (1) | 0.9 (1) | | 4.0 (4) | 1.1 (1) | |

TABLE 6-continued

Amino acid compositions of tryptic peptides from Plt-VI and Plt-VIII

| | Plt-VI | | | | Plt-VIII | | | |
|---|---|---|---|---|---|---|---|---|
| | Tr-5 | Tr-6 | Tr-7 | Tr-8 | Tr-9 | Tr-10 | Tr-11 | Tr-12 |
| Glx | | 4.2 (5) | | 1.7 (2) | | 4.1 (4) | | 1.2 (1) |
| Ser | | | | 1.3 (1) | | | | 1.2 (2) |
| Gly | | 2.9 (3) | | | | 5.4 (4) | | 1.7 (1) |
| His | | | 1.2 (1) | | | 1.1 (1) | 1.0 (1) | |
| Thr | | 0.9 (1) | | 0.7 (1) | | | | 1.1 (1) |
| Ala | 1.2 (1) | | | 1.3 (1) | 1.1 (1) | | | |
| Arg | | 1.2 (1) | | | | 1.6 (1) | | |
| Pro | | 1.0 (1) | 1.0 (1) | | | 1.4 (1) | 1.0 (1) | |
| Tyr | | | | | | | | |
| Val | 1.0 (1) | 1.1 (1) | | | 0.9 (1) | 1.8 (1) | | |
| Met | | 2.3 (2) | | | | 2.5 (2) | | 0.7 (1) |
| Ile | | 2.0 (2) | | | | 2.3 (2) | | |
| Leu | | 1.2 (1) | | | | 1.6 (1) | | |
| Phe | | | | | | | | |
| Lys | 1.0 (1) | | 1.1 (1) | | 1.1 (1) | 1.5 (1) | 0.9 (1) | |
| Trp$^c$ | | (1) | | | | (1) | | |

$^a$Determined from carboxamidomethylated and carboxymethylated fragments.
$^b$Number of residues determined from sequence analysis.
$^c$Not determined.

TABLE 6a

Amino acid compositions of Plt-XI (RCM)$^a$ and fragments from enzyme cleavage: As, Asp-N; Tr, trypsin

| | RCM | As-1 | As-2 | As-3 | As-4 | As-5 | As-6 | As-7 | Tr-13 | Tr-14 | Tr-15 | Tr-16 | Tr-17 |
|---|---|---|---|---|---|---|---|---|---|---|---|---|---|
| ½ Cys | 10.0 (10)$^b$ | 1.0 (1) | 3.3 (3) | 5.3 (5) | 4.6 (4) | 2.0 (2) | 2.6 (3) | 1.0 (1) | 0.1 (0) | 2.0 (2) | 6.0 (6) | 1.1 (1) | 8.6 (8) |
| Asx | 6.6 (6) | 0.1 (0) | 1.3 (1) | 5.0 (5) | 1.3 (1) | 1..8 (2) | 3.3 (3) | 1.2 (1) | 0.1 (0) | 0.1 (0) | 4.4 (5) | 1.0 (1) | 5.2 (5) |
| Glx | 6.7 (7) | 1.9 (2) | 0.9 (1) | 1.9 (2) | 2.4 (3) | 0.1 (0) | 2.0 (2) | 0.5 (0) | 1.3 (1) | 2.0 (2) | 2.2 (2) | 0.1 (0) | 4.4 (4) |
| Ser | 2.0 (2) | 0.2 (0) | 0.2 (0) | 0.9 (1) | 0.2 (0) | 0.2 (0) | 1.7 (1) | 1.5 (1) | 0.1 (0) | 0.2 (0) | 0.2 (0) | 0.1 (0) | 0.4 (0) |
| His | 1.0 (1) | 0.0 (0) | 0.1 (0) | 0.8 (1) | 0.1 (0) | 0.1 (0) | 1.0 (1) | 1.0 (1) | 0.0 (0) | 0.0 (0) | 0.0 (0) | 1.1 (1) | 0.0 (0) |
| Gly | 4.0 (4) | 1.2 (1) | 1.0 (1) | 1.4 (1) | 2.2 (2) | 0.3 (0) | 1.7 (1) | 1.4 (1) | 0.1 (0) | 1.2 (1) | 2.1 (2) | 0.1 (0) | 3.6 (3) |
| Thr | 1.1 (1) | 0.1 (0) | 0.1 (0) | 0.9 (1) | 0.2 (0) | 0.2 (0) | 1.4 (1) | 1.4 (1) | 0.0 (0) | 0.1 (0) | 0.3 (0) | 0.0 (0) | 0.4 (0) |
| Ala | 0.4 (0) | 0.2 (0) | 0.1 (0) | 0.2 (0) | 0.2 (0) | 0.2 (0) | 0.4 (0) | 0.5 (0) | 0.0 (0) | 0.1 (0) | 0.1 (0) | 0.1 (0) | 0.2 (0) |
| Arg | 2.9 (3) | 0.2 (0) | 1.0 (1) | 2.0 (2) | 1.2 (1) | 0.2 (0) | 2.2 (2) | 1.2 (1) | 0.1 (0) | 1.2 (1) | 1.2 (1) | 1.2 (1) | 2.4 (2) |
| Tyr | 1.2 (1) | 0.1 (0) | 1.0 (1) | 0.2 (0) | 1.0 (1) | 0.1 (0) | 0.4 (0) | 0.5 (0) | 0.0 (0) | 1.0 (1) | 0.1 (0) | 0.0 (0) | 1.0 (1) |
| Val | 2.0 (2) | 1.0 (1) | 0.2 (0) | 1.2 (1) | 1.0 (1) | 1.0 (1) | 0.2 (0) | 0.2 (0) | 1.0 (1) | 0.1 (0) | 0.9 (1) | 0.0 (0) | 1.0 (1) |
| Met | 2.0 (2) | 0.1 (0) | 0.1 (0) | 2.3 (2) | 0.1 (0) | 1.0 (1) | 0.9 (1) | 0.2 (0) | 0.0 (0) | 0.0 (0) | 1.9 (2) | 0.0 (0) | 2.2 (2) |
| Ile | 2.9 (3) | 1.0 (1) | 0.1 (0) | 2.0 (2) | 1.0 (1) | 0.0 (0) | 2.0 (2) | 1.0 (1) | 0.0 (0) | 0.9 (1) | 1.0 (1) | 0.0 (0) | 2.0 (2) |
| Phe | 0.2 (0) | 0.1 (0) | 0,0 (0) | 0.1 (0) | 0.1 (0) | 0.0 (0) | 0.1 (0) | 0.1 (0) | 0.0 (0) | 0.0 (0) | 0.0 (0) | 0.0 (0) | 0.0 (0) |
| Leu | 1.2 (1) | 0.1 (0) | 1,0 (1) | 0.1 (0) | 1.1 (1) | 0.1 (0) | 0.3 (0) | 0.1 (0) | 0.0 (0) | 0.0 (0) | 1.0 (1) | 0.0 (0) | 1.2 (1) |
| Lys | 1.1 (1) | 1.0 (1) | 0.1 (0) | 0.2 (0) | 0.9 (1) | 0.1 (0) | 0.2 (0) | 0.5 (0) | 1.0 (1) | 0.0 (0) | 0.0 (0) | 0.0 (0) | 0.0 (0) |
| Pro | 1.8 (2) | 0.3 (0) | 1.0 (1) | 0.9 (1) | 1.1 (1) | 0.3 (0) | 1.2 (1) | 1.6 (1) | 0.0 (0) | 0.1 (0) | 1.2 (1) | 1.0 (1) | 1.6 (1) |
| Trp$^c$ | (1) | (1) | (0) | (0) | (1) | (0) | (0) | (0) | (0) | (1) | (0) | (0) | (1) |

$^a$Reduced, carboxymethylated (RCH).
$^b$Number of residues from sequence analysis.
$^c$Not determined.

TABLE 7

ABUNDANCE OF VARIOUS PLTS IN VENOM

| | nmol toxin/μl venom | μg toxin/μl venom |
|---|---|---|
| Plt-V | 0.17 | 0.86 |
| Plt-VI | 0.067 | 0.34 |
| Plt-VIII | 0.14 | 0.70 |
| Plt-IX | 0.099 | 0.50 |
| Plt-X | 0.24 | 1.24 |
| Plt-XI | 0.03 | 0.13 |

EXAMPLE 2

Bioactivity of Various Plectoxins

Various plectoxins isolated from venom are injected into three different insect larvae. Results are presented below. $LD_{50}$ is the lethal dose for 50% of the treated larvae at 24 hours. $ED_{50}$ is the dose which is effective to paralyze 50% of the larvae at one hour. Values with an asterisk denote duplicate analysis with samples from different milking lots.

TABLE 8

| | Toxicity (μL/g for venom; μg/g for toxins) | | | | | |
|---|---|---|---|---|---|---|
| | M. sexta | | H. virescens | | S. exigua | |
| | LD$_{50}$ | ED$_{50}$ | LD$_{50}$ | ED$_{50}$ | LD$_{50}$ | ED$_{50}$ |
| Venom | 0.036* | 0.025* | 0.088* | 0.065* | 0.10 | 0.064 |
| Plt-V | 0.07* | 0.04* | 21.6* | 0.52* | >10* | 0.44* |
| Plt-VI | 0.15* | 0.10* | 1.2* | 0.21* | >10* | 0.32* |
| Plt-VIII | 0.9 | 0.42 | >10 | 1.89 | >5 | >5 |
| Plt-IX | >11 | >11 | >11 | >11 | | |
| Plt-X | >10 | >10 | 3.5 | >10 | 8.0 | 13 |
| Plt-XI | >1 | 0.36 | >2 | 1.38 | >1 | 0.24 |

*Duplicate analysis with samples from different milking lots

EXAMPLE 3

Isolation of mRNA

Live *P. tristis* spiders (Spider Pharm, Black Canyon City, Ariz.) are quickly frozen in liquid nitrogen and the legs and abdomens are separated from the cephalothoraces. 25 cephalothoraces (1 gram) are homogenized with a Polytron homogenizer for 1 minute in 20 ml of RNA extraction buffer (4M guanidine isothiocyanate, 50 mM sodium citrate, pH 7.0, and 0.1M 2-mercaptoethanol). Following homogenization, 1 ml of 10% Sarkosyl is added. The homogenate is centrifuged at 8000 rpm for 10 minutes at 4° C. in a Sorvall HB-4 rotor, and the supernatants are decanted into clean tubes to remove insoluble debris. This is repeated twice, and then 0.025 volumes (0.5 ml) of 1M acetic acid and 0.75 volumes (15 ml) of 100% ethanol are mixed into the cleared lysate, which is stored at −20° C. overnight. After centrifugation at 10,000 rpm for 10 minutes at 4° C. using a HB-4 rotor, the supernatant is discarded and the pellet is resuspended in 15 ml of FastTrack (Invitrogen Corp.) lysis buffer. Approximately 8 μg of poly A+ cephalothorax mRNA is then isolated following the protocol provided by the manufacturer (Invitrogen Corp.) for the FastTrack mRNA isolation kit.

EXAMPLE 4

PCR Amplification

Single-stranded cDNA is synthesized from the isolated mRNA of Example 3 (0.5 μg) using M-MLV reverse transcriptase (GIBCO-Bethesda Research Laboratories) primed with a degenerate 30-mer oligonucleotide primer with the following sequence (SEQ. ID. NO.:12):

5'-GATGCGGCCGCTC[G,A]CA[C,T]TC[G,A]TT[[C,G,T,A]GT [C,G,T,A]GC[C,T]TT[C,G,T,A]GG-3'.

This primer contains a NotI sequence within the first 11 nucleotides followed by 19 nucleotides complementary to a sequence derived by reverse translation of the Plt-VI plectoxin amino acid sequence. Following the cDNA synthesis, the reactions are heated to 90° C. for 5 min, cooled to room temperature and ethanol precipitated. The cDNA reaction product is amplified in a 100 μl reaction with PCR geneAMP reagents (Perkin-Elmer Cetus Instruments) using 2 μM each of the above primer and another degenerative primer with the following sequence (SEQ. ID. NO.:13):

5'GATGCGGCCGCGT[C,G,T,A]AA[G,A]TG[C,T]AT[G,T,A]GG [C,G,T,A]TGGC-3'

This second primer also contains a NotI site in the first 11 nucleotides followed by a sequence corresponding to a portion of the reverse translation product of the Plt VI plectoxin amino acid sequence. PCR conditions are: 1 min at 94° C., 2 min at 37° C., slow increase of the temperature over 3 min to 72° C., 3 min at 72° C., 10 second extension of the 72° C. segment/cycle for 30 cycles, and a final cycle extension of 72° C. segment for 10 minutes.

DNA fragments with the expected size of approximately 130 bp are produced. These are gel purified, cloned into pTZ18R (BIO-RAD Laboratories) and four clones are sequenced. One of these clones contains a reading frame that matches the amino acid sequence of mature Plt-VI.

TABLE 9

The amino acid sequence of mature Plt-VI (SEQ. ID. NO.:5) is shown on line 1. The nucleotide sequence derived by reverse translation of the Plt-VI amino acid sequence (SEQ. ID. NO.:14) is shown below the amino acid sequence. All possible nucleotides at each position are indicated. Y = C or T; R = A or G; M = A or C; W = A or T; H = A, C, or T; N = A, T, C, or G. Degenerate oligonucleotides corresponding to the first underlined region and the complement of the second underlined region are used as PCR primers for amplification from Plt-VI cephalothorax mRNA. The nucleotide sequence from a cloned PCR fragment is shown on line 3 (SEQ. ID. NO.:15). There is an out-of-frame C in the nucleotide sequence following the His codon at amino acid position 37, presumably arising as a PCR artifact. Lower case letters correspond to primer regions.

| | | | | | 5 | | | | | 10 | | | | | 15 |
|---|---|---|---|---|---|---|---|---|---|---|---|---|---|---|---|
| 1 | Ala | Val | Lys | Cys | Ile | Gly | Trp | Gln | Glu | Thr | Cys | Asn | Gly | Asn | Leu |
| 2 | CGN | GTN | AAR | TGY | ATH | GGN | TGG | CAR | GAR | ACN | TGY | AAY | GGN | AAY | YTN |
| 3 | | gtt | aag | tgt | att | ggt | tgg | cAG | GAA | ACA | TGC | AAC | GGC | AAC | TTG |

| | | | | | 20 | | | | | 25 | | | | | 30 |
|---|---|---|---|---|---|---|---|---|---|---|---|---|---|---|---|
| 1 | Pro | Cys | Cys | Asn | Glu | Cys | Val | Met | Cys | Glu | Cys | Asn | Ile | Met | Gly |
| 2 | CCN | TGY | TGY | AAY | GAR | TGY | GTN | ATG | TGY | GAR | TGY | AAY | ATH | ATG | GGN |
| 3 | CCC | TGC | TGC | AAT | GAG | TGC | GTC | ATG | TGC | GAA | TGC | AAC | ATT | ATG | GGT |

TABLE 9-continued The amino acid sequence of mature Plt-VI (SEQ. ID. NO.:5) is shown on line
1. The nucleotide sequence derived by reverse translation of the Plt-VI amino
acid sequence (SEQ. ID. NO.:14) is shown below the amino acid sequence. All
possible nucleotides at each position are indicated. Y = C or T; R = A or G;
M = A or C; W = A or T; H = A, C, or T; N = A, T, C, or G. Degenerate
oligonucleotides corresponding to the first underlined region and the complement of
the second underlined region are used as PCR primers for amplification from Plt-VI
cephalothorax mRNA. The nucleotide sequence from a cloned PCR fragment is
shown on line 3 (SEQ. ID. NO.:15). There is an out-of-frame C in the nucleotide
sequence following the His codon at amino acid position 37, presumably arising
as a PCR artifact. Lower case letters correspond to primer regions.

```
              35                       40                      45
1  Gln Asn Cys Arg Cys Asn His Pro Lys Ala Thr Asn Glu Cys Glu Ser
2  CAR AAY TGY MGN TGY AAY CAY CCN AAR GCN ACN AAY GAR TGY GAR WSN
3  CAA AAC TGC AGA TGC AAC CATccg aaa gcg acc aat gaa tgt ga
```

EXAMPLE 5 cDNA Synthesis and Cloning

The lambda phage λZAPII system (Stratagene Corp) is used for cDNA synthesis and cloning starting with 3.5 µg P. tristis cephalothorax mRNA. The oligonucleotide 5'-GGATGGTTGCATCTGCAG-3' (SEQ. ID. NO.:16) is end-labelled at the 5'-end with $^{32}P$ using polynucleotide kinase (Sambrook et al, 1989 *Molecular Cloning: A Laboratory Manual, Second Edition* Cold Spring Harbor Laboratory Press, Cold Spring Harbor, N.Y.), and is used as a probe for screening the *P. tristis* cephalothorax cDNA library by plaque hybridization (Sambrook et al, supra). 73 positive plaques are detected in a library screening of approximately $1\times10^6$ plaques.

DNA sequencing and sequence analysis. Double stranded pBluescript SK$^-$ (Stratagene) plasmid DNA containing cDNA inserts of nine clones is generated from λZAPII cDNA clones using the in vivo procedure described in the λZAPII instruction manual. The cDNA inserts are sequenced in both directions using M13 and M13 reverse primers and the Pharmacia LKB $^{T7}$DNA Sequencing Kit according to the manufacturer's instructions, and is given in TABLES 10–11. The nucleotide sequences and predicted protein sequences are analyzed with the IntelliGenetics computer programs.

Primer extension. In order to determine the expected size of a full length cDNA, a primer extension reaction is performed on the *P.tristis* cephalothorax mRNA. The transcriptional initiation site of Plt-VI mRNA is confirmed by primer extension analysis using the following 31-mer oligonucleotide (SEQ. ID. NO.:17): 5'-GTGCAAACGA CCAATGCACA GACAAGGGCG G-3', which is complementary to a portion of the Plt-VI mRNA. The oligonucleotide is 5'-end labeled with T4 polynucleotide kinase (Sambrook et al, supra). Primer annealing and primer extension reactions are performed essentially as described by Blissard, G. W. and G. F. Rohrmann, 1989 *Virology* 170:537–555, which is hereby incorporated by reference, except that the extension reactions contain 10 mM Tris (pH 8.0) and 2.5 μg of *P. tristis* cephalothorax mRNA. The sizes of the primer extension products are determined by comparison against a sequencing ladder produced from pBluescriptII SK$^+$ (Stratagene) using the M13–20 primer. Two major bands and several minor bands approximately 20–30 bp larger than the major bands are detected.

Analysis of the largest cDNA clone, pSC1263, reveals that it is several bases longer at the N-terminus than predicted for full length cDNA based on the sizes of the major primer extension products, suggesting that it may be derived from an mRNA which initiates at one of the positions indicated by the minor bands. The remaining eight cDNAs are much shorter than full length. All nine clones contain putative polyadenylation signals (AATAAA) near the 3' terminus (Proudfoot and Brownlee, 1976. *Nature* 263:211–214). In six of the nine clones, the poly(A+) tail is positioned 20 bp downstream from the beginning of the polyadenylation signal, and in 3 clones the poly(A+) tail is positioned an additional 3 to 21 bases further downstream.

EXAMPLE 6

Baculovirus Construction

Construction of AcNPV p10 gene based transfer vectors containing Plt-VI cDNA. Reference is made to FIGS. 3a, 3b, 4a and 4b. The cDNA insert of clone pSCI266 is removed by cutting with EcoRI and XhoI. After gel purification, the single stranded DNA ends are filled in by treatment with the Klenow fragment of *E. coli* DNA polymerase I in the presence of all four dNTPs. Plasmid pACJJ2 (obtained from Dr. Just Vlak, Dept. of Virology, Agricultural Univ., Wageningen, The Netherlands) which has a polylinker in place of the complete p10 open reading frame is cut with BamHI, the ends are filled, phosphatased with calf intestinal phosphatase, and then is ligated with the cDNA from pSCI266 to form pSCI183.

The construction of plasmid pSCI184 is similar to that described above for pSCI183, except the cDNA insert is from pSCI270.

Plasmid pSCI185 which contains the cDNA from clone pSCI266 inserted downstream from a hybrid p10-capsid-polyhedrin promoter is constructed as follows. A fragment containing the hybrid capsid-polyhedrin promoter is removed from pCappolh (Thiem and Miller, 1990. Gene 91:87–94) by cutting with EcoRV and BglII. The BglII-cut sticky end is filled in and the fragment is cloned into pAcJJ2 which is cut with BamHI, filled in, and phosphatased to form pSCI181. pSCI181 is then cleaved with SmaI, phosphatased and is ligated with the cDNA fragment from pSCI266 described above to form pSCI185.

Plasmid pSCI198, which contains the cDNA from clone pSCI266 downstream from the hybrid capsid-polyhedrin promoter is constructed as follows. The AcNPV fragments EcoRI-P and EcoRI-X are subcloned separately into pTZ18R to form pSCI206 and pSCI250, respectively. pSCI206 is partially cut with EcoRI, the ends filled in by the Klenow reaction, and then religated to form pSCI176. The EcoRI-X fragment is then cloned from pSCI250 into pSCI176 to form pSCI177. pSCI177 is then partially cut with HindIII, the ends are filled by the Klenow reaction, and then is religated to form pSCI178. An EcoRV site in place of the p10 ATAAG transcriptional initiation site is introduced by in vitro mutagenesis of pSCI177 using a primer with the following sequence (SEQ. ID. NO.:36):

5'-CAATATATTATAGTTAAGATATCAATTATTATCAAATC-3' and the resulting plasmid is designated pSCI186. pSCI186 is then cut with EcoRV and BglII, phosphatased and then is ligated to an EcoRV-BglII fragment containing the hybrid capsid-polyhedrin promoter from pCapPolhcat (Thiem and Miller, supra) to form pSCI187. pSCI187 is cut with BglII, ends are filled in and phosphatased, and then are ligated to the cDNA fragment from pSCI266 (above) to form pSCI198.

EXAMPLE 7

Bioassays

The genetically engineered baculovirus containing a plectoxin is bioassayed according to the procedure of Stewart et al, 1991, *Nature* 352:85, which is hereby incorporated by reference. Briefly, to measure $LD_{50}$: Fifty second-instar *H. virescens* larvae (about 0.6–0.7 mg) are individually fed five dilutions of each virus stock on a small plug of artificial diet in a microtitre plate. The maximum dose of the virus is chosen so that it results in over 90% mortality, and the minimum dose results in about 10% mortality. For non-engineered AcNPV, these amounts are approximately 120, 60, 30, 15 and 7.5 polyhedra per larva. Larvae that consume the dose in 24 hours are transferred to individual containers of artificial diet and are examined daily. Cadavers are removed, smeared on a slide and the cause of death is confirmed. The data are analyzed using probit analysis to determine the $LD_{50}$ values.

To determine survival time ($ST_{50}$), the following procedure is used. Adults are reared in cages containing filter papers for oviposition. Filters carrying eggs are surface sterilized and retained in plastic containers. After hatching, the neonates are starved for 3–6 hr before droplet feeding with each virus suspension ($2\times10^6$ polyhedra per ml). The suspensions are colored with 5% blue food dye to allow visualization of feeding. Small droplets of virus are placed on a Petri dish in concentric rings. The larvae are put in the center of the rings, after which they move through the droplets, taking in a small volume of liquid before crawling on to the lid of the dish. After feeding, larvae are maintained in individual containers with artificial diet at 23° C. After 24 h, the larvae killed by handling are removed. Thereafter the larvae are checked at frequent intervals. Dead larvae are removed and the cause of death diagnosed by appearance and microscopic examinations. $ST_{50}$ calculations are made with the Vistat program.

The larvae infected with the virus carrying the plectoxin gene show lower $ST_{50}$ scores.

---

What is claimed is:

1. An isolated and purified DNA encoding a polypeptide, free from associated arachnoidal polypeptides, comprising the following amino acid sequence (SEQ. ID. NO.:1; Formula A):

$$AA_1\text{-}AA_2\text{-}Lys\text{-}Cys\text{-}AA_5\text{-}Gly\text{-}Trp\text{-}AA_8\text{-}AA_9\text{-}AA_{10}\text{-}Cys\text{-}AA_{12}\text{-}Gly\text{-}AA_{14}\text{-}AA_{15}\text{-}AA_{16}\text{-}Cys\text{-}Cys\text{-}AA_{19}\text{-}AA_{20}\text{-}Cys\text{-}Val\text{-}Met\text{-}AA_{24} \quad (A)$$

wherein $AA_1$ is Ala or Glu; $AA_2$ is Val or Leu; $AA_5$ is Ile or Gln; $AA_8$ is Gln or Val; $AA_9$ is Glu or Asp; $AA_{10}$ is Thr or Tyr; $AA_{12}$ is Asn or Arg; $AA_{14}$ is Asn or Lys; $AA_{15}$ is Leu or Val; $AA_{16}$ is Pro or Glu; $AA_{19}$ is Asn or Asp; $AA_{20}$ is Glu, Gly, or Asp; and $AA_{24}$ is Cys or Tyr; or a polypeptide comprising the sequence of Formula A and further comprising the following additional amino acids after $AA_{24}$ (SEQ. ID. NO.:2; Formula B):

$$\text{-}Glu\text{-}Cys\text{-}Asn\text{-}Ile\text{-}Met\text{-}Gly\text{-}Gln\text{-}Asn\text{-}Cys\text{-}Arg\text{-}Cys\text{-}Asn\text{-}His\text{-}Pro\text{-}AA_{39}\text{-}AA_{40}\text{-}Thr\text{-}AA_{42} \quad (B)$$

wherein $AA_{39}$ is Lys or Arg; $AA_{40}$ is Ala, Met, or Ile; and $AA_{42}$ is Asn or Ser; or a polypeptide comprising the sequence of Formula B and further comprising an additional Glu after $AA_{42}$ (Formula C); or a polypeptide comprising the sequence of Formula C and further comprising the following additional amino acid sequence following the Glu at position 43 (Formula D):

$$\text{-}Cys\text{-}AA_{45} \quad (D)$$

wherein $AA_{45}$ is Glu or Gly; or a polypeptide comprising the sequence of Formula D and further comprising a Ser after $AA_{45}$; (Formula E) or a polypeptide of the Formula F comprising the following amino acid sequence (SEQ. ID. NO.:3):

Cys-Ala-Lys-His-Ser-Glu-Thr-Cys-Lys-Asn-Gly-Asn-Cys-Cys-Thr-Cys-Thr-Gln-Tyr-Arg-Gly-Lys-Asp-Glu-Pro-Met-Ala-Cys-Arg-Arg-Gly-Thr-His-Gly-Gln-Arg-Cys-Gln-Cys-Val-Met-Lys-Ile-Met-Lys-His    (F)

or a polypeptide of the Formula G comprising the following amino acid sequence (SEQ. ID. NO.:4):

Gly-Cys-Lys-Gly-Phe-Leu-Val-Lys-Cys-Asp-Ser-Asn-Ser-Glu-Cys-Cys-Lys-Thr-Ala-Ile-Val-Lys-Gly-Lys-Lys-Lys-Gln-Leu-Ser-Cys-Leu-Cys-Gly-Ala-Trp-Gly-Ala-Gly-Cys-Ser-Cys-Ser-Phe-Arg-Cys-Gly-Asn-Arg-Cys-OH    (G)

or homologous polypeptides of Formula A–G, wherein the cysteine residues of said homologous peptide is identical to the number and position of the cysteine residues of one of the polypeptides of Formula A–G and wherein the complementary strand of the DNA molecule encoding said homologous peptide will hybridize to the DNA molecule encoding one of the polypeptides of Formula A–G under stringent hybridization conditions.

2. A DNA molecule according to claim 1 which comprises nucleotides which encode a polypeptide of formula E wherein $AA_1$ is Ala; $AA_2$ is Val; $AA_5$ is Ile; $AA_8$ is Gln; $AA_9$ is Glu; $AA_{10}$ is Thr; $AA_{12}$ is Asn; $AA_{14}$ is Asn or Lys; $AA_{15}$ is Leu; $AA_{16}$ is Pro; $AA_{19}$ is Asn or Asp; $AA_{20}$ is Glu or Gly; $AA_{24}$ is Cys; $AA_{39}$ is Lys; $AA_{40}$ is Ala or Met; $AA_{42}$ is Asn or Ser; and $AA_{45}$ is Glu or Gly.

3. A DNA molecule according to claim 1 which comprises nucleotides which encode a polypeptide of Formula E wherein $AA_1$=Glu, $AA_2$=Val, $AA_5$=Ile, $AA_8$=Gln, $AA_9$=Glu, $AA_{10}$=Tyr, $AA_{12}$=Arg, $AA_{14}$=Asn, $AA_{15}$=Leu, $AA_{16}$=Pro, $AA_{19}$=Asp; $AA_{20}$=Asp, $AA_{24}$=Cys, $AA_{39}$=Arg, $AA_{40}$=Ile, $AA_{42}$=Ser, and $AA_{45}$=Gly.

4. A recombinant baculovirus comprising a gene construct comprising a baculovirus promoter operably linked to a DNA sequence encoding a polypeptide according to claim 1.

5. A baculovirus according to claim 4 wherein the baculovirus promoter is a p10 promoter.

6. A baculovirus according to claim 5 wherein the polypeptide is Plt-VI.

7. A method of controlling insects comprising: infecting the insects with a recombinant virus, said virus comprising a gene construct which comprises a baculovirus promoter operably linked to a DNA sequence encoding a polypeptide according to claim 1.

8. A cloning vector comprising a DNA molecule according to claim 1.

\* \* \* \* \*